(12) United States Patent
Zeman et al.

(10) Patent No.: US 8,078,263 B2
(45) Date of Patent: Dec. 13, 2011

(54) PROJECTION OF SUBSURFACE STRUCTURE ONTO AN OBJECT'S SURFACE

(75) Inventors: Herbert D. Zeman, Memphis, TN (US);
Gunnar Lovhoiden, Bartlett, TN (US);
Carlos Vrancken, Memphis, TN (US);
John Snodgrass, Denton, TX (US);
James A. DeLong, Shady Shores, TX (US)

(73) Assignee: Christie Medical Holdings, Inc., Cypress, CA (US)

( * ) Notice: Subject to any disclaimer, the term of this patent is extended or adjusted under 35 U.S.C. 154(b) by 578 days.

(21) Appl. No.: 11/173,452

(22) Filed: Jul. 1, 2005

(65) Prior Publication Data

US 2006/0122515 A1 Jun. 8, 2006

Related U.S. Application Data

(63) Continuation-in-part of application No. 10/386,249, filed on Mar. 11, 2003, now Pat. No. 7,239,909, which is a continuation-in-part of application No. 09/487,007, filed on Jan. 19, 2000, now Pat. No. 6,556,858.

(51) Int. Cl.
*A61B 6/00* (2006.01)
(52) U.S. Cl. ......... 600/473; 600/309; 600/310; 600/322
(58) Field of Classification Search .......... 600/473–476, 600/309, 310, 323, 322
See application file for complete search history.

(56) References Cited

U.S. PATENT DOCUMENTS

| | | | |
|---|---|---|---|
| 3,693,025 A | 9/1972 | Brunton | |
| 3,892,492 A | 7/1975 | Eichenberger | |
| 4,699,149 A | 10/1987 | Rice | |
| 4,817,622 A * | 4/1989 | Pennypacker et al. | 600/473 |
| 4,893,223 A | 1/1990 | Arnold | |
| 4,908,876 A | 3/1990 | DeForest et al. | |
| 4,945,253 A | 7/1990 | Frohardt | |
| 4,947,850 A | 8/1990 | Vanderkooi et al. | |

(Continued)

FOREIGN PATENT DOCUMENTS

DE 20115964 U1 3/2003

(Continued)

OTHER PUBLICATIONS

H.D. Zeman, G. Lovhoiden, and C. Vrancken, Prototype Vein Contrast Enhancer, Proc. of SPIE (Jul. 1, 2004; USA).

(Continued)

*Primary Examiner* — Brian Casler
*Assistant Examiner* — Nasir Shahrestani
(74) *Attorney, Agent, or Firm* — Butler, Snow, O'Mara, Stevens & Cannada PLLC

(57) ABSTRACT

An imaging system illuminates an object with infrared light to enhance visibility of buried structure beneath the surface of the object, and projects a visible light image of the buried structure onto the surface of the object. The system may include an infrared light source for generating the infrared light and a structure for diffusing the infrared light. The diffusing structure may include one or more layers of diffusing material for diffusing the light. The system further includes a video imaging device for receiving the infrared light reflected from the object and for generating a video image of the buried structure based on the reflected infrared light. The buried structure may be a subcutaneous blood vessel. A calibration procedure is described as well as embodiments for ensuring that the object is maintained in focus at the correct distance.

6 Claims, 30 Drawing Sheets

U.S. PATENT DOCUMENTS

| | | | |
|---|---|---|---|
| 5,041,965 A | 8/1991 | Chen | |
| 5,073,714 A | 12/1991 | Nguyen | |
| 5,087,822 A | 2/1992 | Fairlie et al. | |
| 5,159,361 A | 10/1992 | Cambier et al. | |
| 5,185,638 A | 2/1993 | Conzola et al. | |
| 5,231,434 A | 7/1993 | Kennedy et al. | |
| 5,291,560 A | 3/1994 | Daugman | |
| 5,353,075 A | 10/1994 | Conner et al. | |
| 5,359,550 A | 10/1994 | Chen | |
| 5,367,439 A | 11/1994 | Mayer et al. | |
| 5,424,838 A | 6/1995 | Siu | |
| 5,477,284 A * | 12/1995 | Taylor et al. | 353/122 |
| 5,477,332 A | 12/1995 | Stone et al. | |
| 5,497,266 A | 3/1996 | Owen | |
| 5,514,864 A | 5/1996 | Mu-Tung et al. | |
| 5,519,208 A * | 5/1996 | Esparza et al. | 250/226 |
| 5,543,865 A | 8/1996 | Nanjo | |
| 5,598,842 A * | 2/1997 | Ishihara et al. | 600/322 |
| 5,603,328 A | 2/1997 | Zucker et al. | |
| 5,608,210 A * | 3/1997 | Esparza et al. | 250/226 |
| 5,678,555 A | 10/1997 | O'Connell | |
| 5,757,544 A | 5/1998 | Tabata et al. | |
| 5,772,593 A * | 6/1998 | Hakamata | 600/407 |
| 5,787,185 A | 7/1998 | Clayden | |
| RE36,044 E | 1/1999 | Benaron | |
| 5,907,395 A | 5/1999 | Schulz et al. | |
| 5,947,906 A | 9/1999 | Dawson, Jr. et al. | |
| 5,969,754 A | 10/1999 | Zeman | |
| 6,032,070 A * | 2/2000 | Flock et al. | 600/473 |
| 6,101,038 A | 8/2000 | Hebert et al. | |
| 6,178,340 B1 * | 1/2001 | Svetliza | 600/310 |
| 6,219,572 B1 | 4/2001 | Young | |
| 6,230,046 B1 * | 5/2001 | Crane et al. | 600/476 |
| 6,251,100 B1 | 6/2001 | Flock et al. | |
| 6,301,375 B1 | 10/2001 | Choi | |
| 6,314,311 B1 * | 11/2001 | Williams et al. | 600/425 |
| 6,353,753 B1 | 3/2002 | Flock et al. | |
| 6,374,128 B1 | 4/2002 | Toida et al. | |
| 6,433,760 B1 | 8/2002 | Vaissie et al. | |
| 6,438,396 B1 | 8/2002 | Cook et al. | |
| 6,464,646 B1 | 10/2002 | Shalom et al. | |
| 6,556,858 B1 | 4/2003 | Zeman | |
| 6,574,432 B2 | 6/2003 | Nanjyo | |
| 6,650,916 B2 | 11/2003 | Cook et al. | |
| 6,813,010 B2 | 11/2004 | Kono | |
| 7,239,909 B2 | 7/2007 | Zeman | |
| 2004/0022421 A1 | 2/2004 | Endoh et al. | |
| 2004/0064057 A1* | 4/2004 | Siegel | 600/500 |
| 2004/0111030 A1 | 6/2004 | Zeman | |
| 2004/0207625 A1* | 10/2004 | Griffin et al. | 345/440 |
| 2005/0281438 A1 | 12/2005 | Zhang et al. | |
| 2006/0122515 A1 | 6/2006 | Zeman et al. | |

FOREIGN PATENT DOCUMENTS

| | | |
|---|---|---|
| EP | 0 678 002 A1 | 10/1995 |
| EP | 1 065 969 B1 | 6/2002 |
| JP | 2172472 | 7/1990 |
| JP | 2172473 | 7/1990 |
| JP | 2174852 | 7/1990 |
| JP | 2174853 | 7/1990 |
| JP | 2174854 | 7/1990 |
| WO | WO 9415531 A1 | 7/1994 |
| WO | WO 99/48420 A1 | 3/1997 |
| WO | WO 98/26583 A1 | 6/1998 |
| WO | WO 97/08537 A1 | 9/1999 |
| WO | WO 01/54393 A2 | 7/2001 |

OTHER PUBLICATIONS

G. Lovhoiden, H. Deshmukh, C. Vrancken, Y. Zhang, H.D. Zeman, D. Winberg: Commercialization of Vein Contrast Enhancement, Proc. of SPIE, Biomedical Optics (Jul. 22, 2003; USA).

G. Lovhoiden, H. Deshmukh, and H.D. Zeman, Clinical Evaluation of Vein Contrast Enhancement, Proc. of SPIE, vol. 4615, Biomedical Optics, 2002, pp. 61-67, USA.

H.D. Zeman, G. Lovhoiden, and H. Deshmukh, Design of a Clinical Vein Contrast Enhancing Projector, Proc. of SPIE, vol. 4254, pp. 204-215, Jun. 2001; USA.

H.D. Zeman, G. Lovhoiden, and H. Deshmukh, Optimization of Subcutaneous Vein Contrast Enhancement, Proc. of SPIE, vol. 3911, pp. 50-57, May 2000; USA.

H.D. Zeman and G. Lovhoiden, Enhancing the Contrast of Subcutaneous Veins, Proc. of SPIE, vol. 3595, pp. 219-230, Jul. 1999; USA.

H.D. Zeman et al.: The Clinical Evaluation of Vein Contrast Enhancement, Proceedings of the IEEE/EMBS Sep. 2004.

H. Deshmukh, Vein Contrast Enhancement Using Diffuse Infrared Light, Masters Thesis, University of Tennessee, Health Science Center, 2002 (111 pages); USA.

Peli et al., Image Enhancement for the Visually Impaired, Investigative Ophthalmology & Visual Science, vol. 32, No. 8, Jul. 1991, pp. 2337-2350.

In Focus Systems, LitePro 620, Specifications, http://www.infocus.com/Support/Products/Projectors/LP620.aspx (4 pages), date unknown; USA.

In Focus Systems, LitePro 620, Quick Start, http://www.infocus.com/Support/Products/Projectors/LP620.aspx (2 pages), date unknown; USA.

In Focus Systems, LitePro 620, LP610-LP620 Reference Guide, http://www.infocus.com/Support/Products/Projectors/LP620.aspx, pp. i-v, 1-67, date unknown; USA.

R.J. Gove, DMD Display Systems: The Impact of an All-Digital Display, http://www.ti.com/dlp/docs/papers/state/state.htm (date unknown); Texas Instruments, USA.

Basler Vision Technologies, Basler A600-HDR Product Specifications, Jan. 2004 (2 pages), Germany.

Basler Vision Technologies, Basler A600 Series Cameras, http://www.baslerweb.com/produkte/produkte_en_1455.php (2 pages), Germany, date unknown.

Basler Vision Technologies, Basler A601f-HDR User's Manual http://www.baslerweb.com/beitraege/beitrag_en_17681.html, (Mar. 22, 2004) entire document—110 pages, Germany.

Intel Integrated Performance Primitives for Intel Architecture, Reference Manual, vol. 2, Document No. A70805-014, entire document—1264 pages, Jul. 2004; USA.

G. Lovhoiden, Design of a Prototype Vein Enhancing Illuminator, Ph.D. Thesis, U.Tenn., Health Sci. Ctr., (cover, pp. i-iv, 1-243) (cataloged/publ. by U.Tenn. Jul. 9, 2004) USA.

* cited by examiner

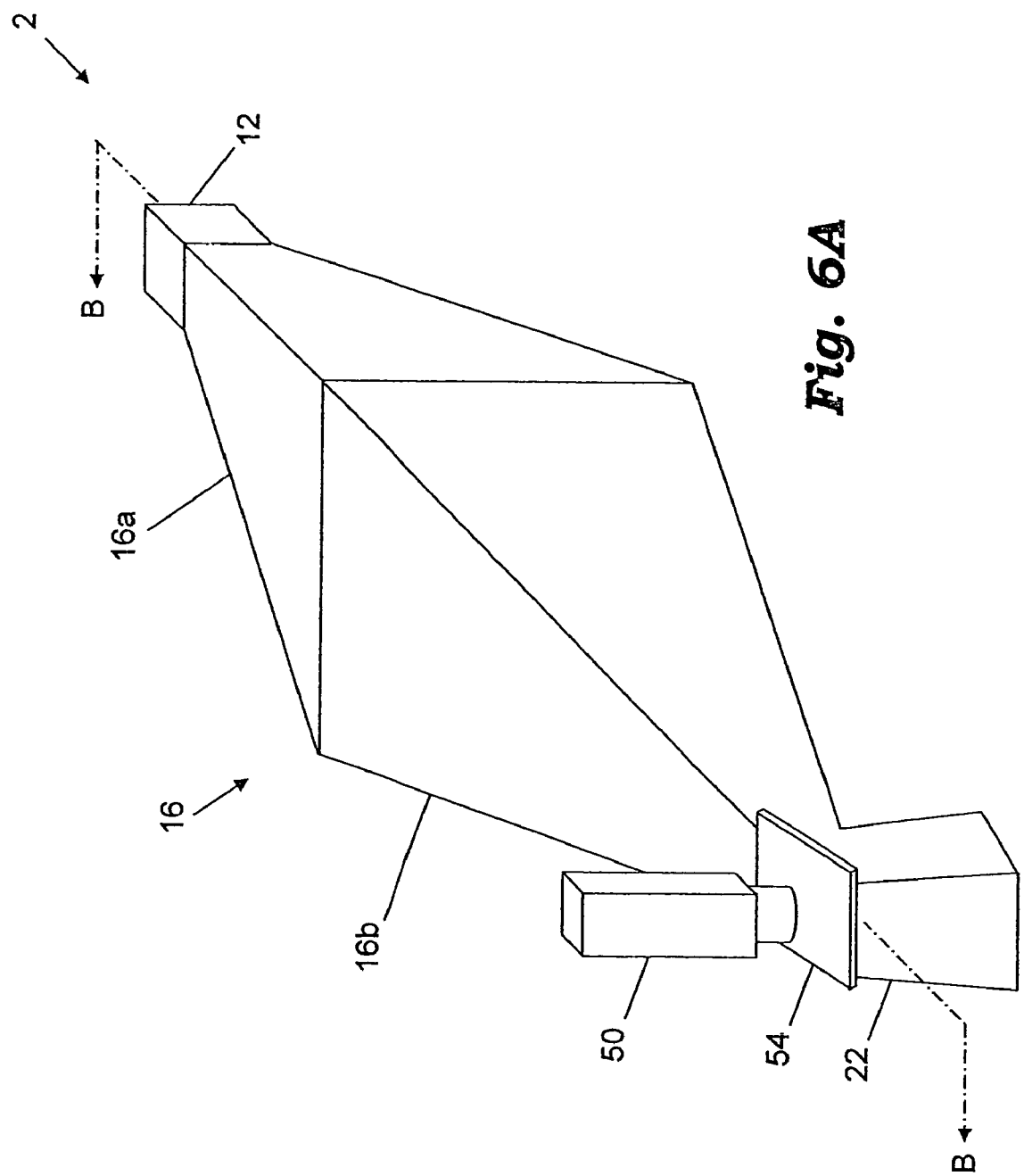

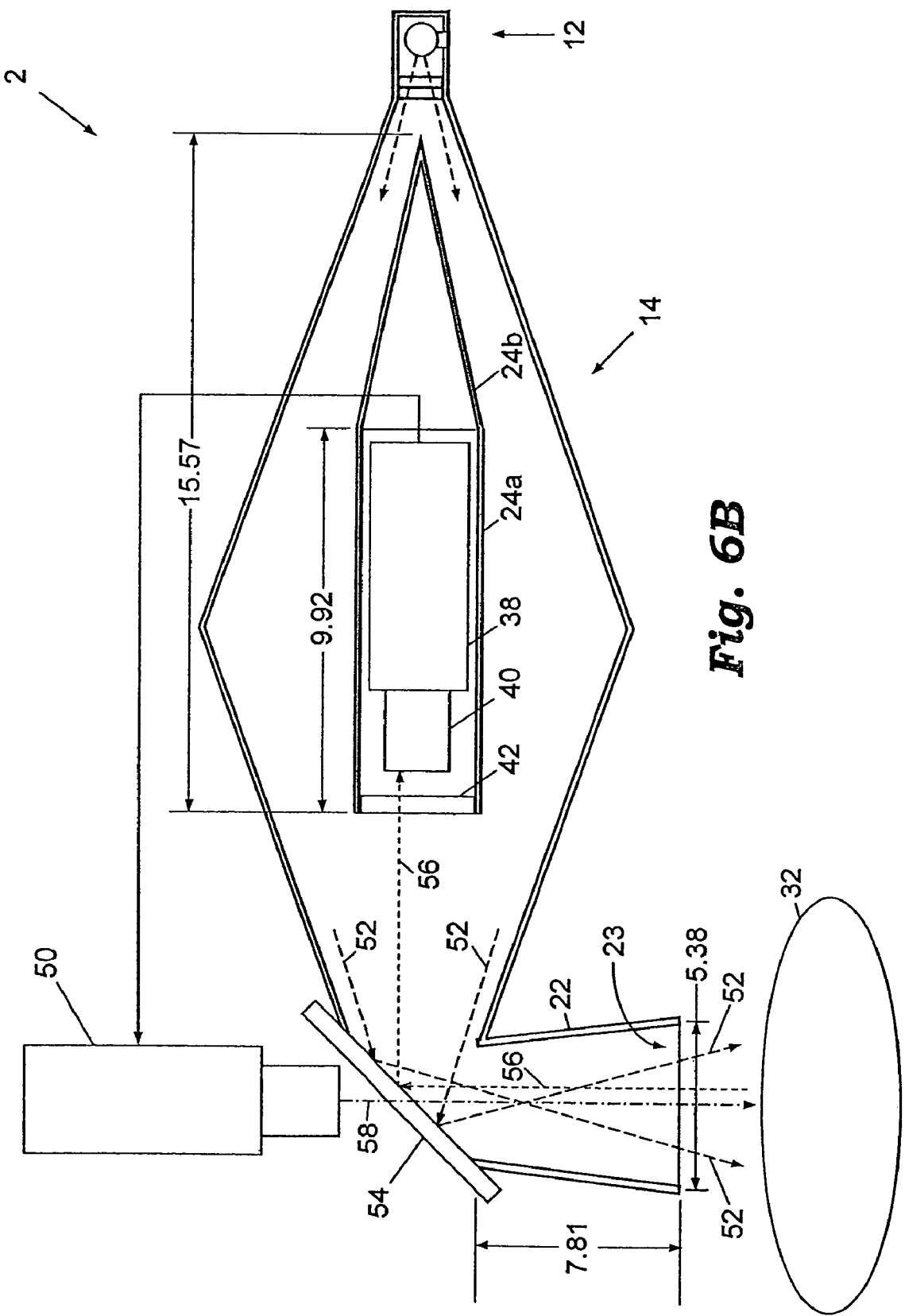

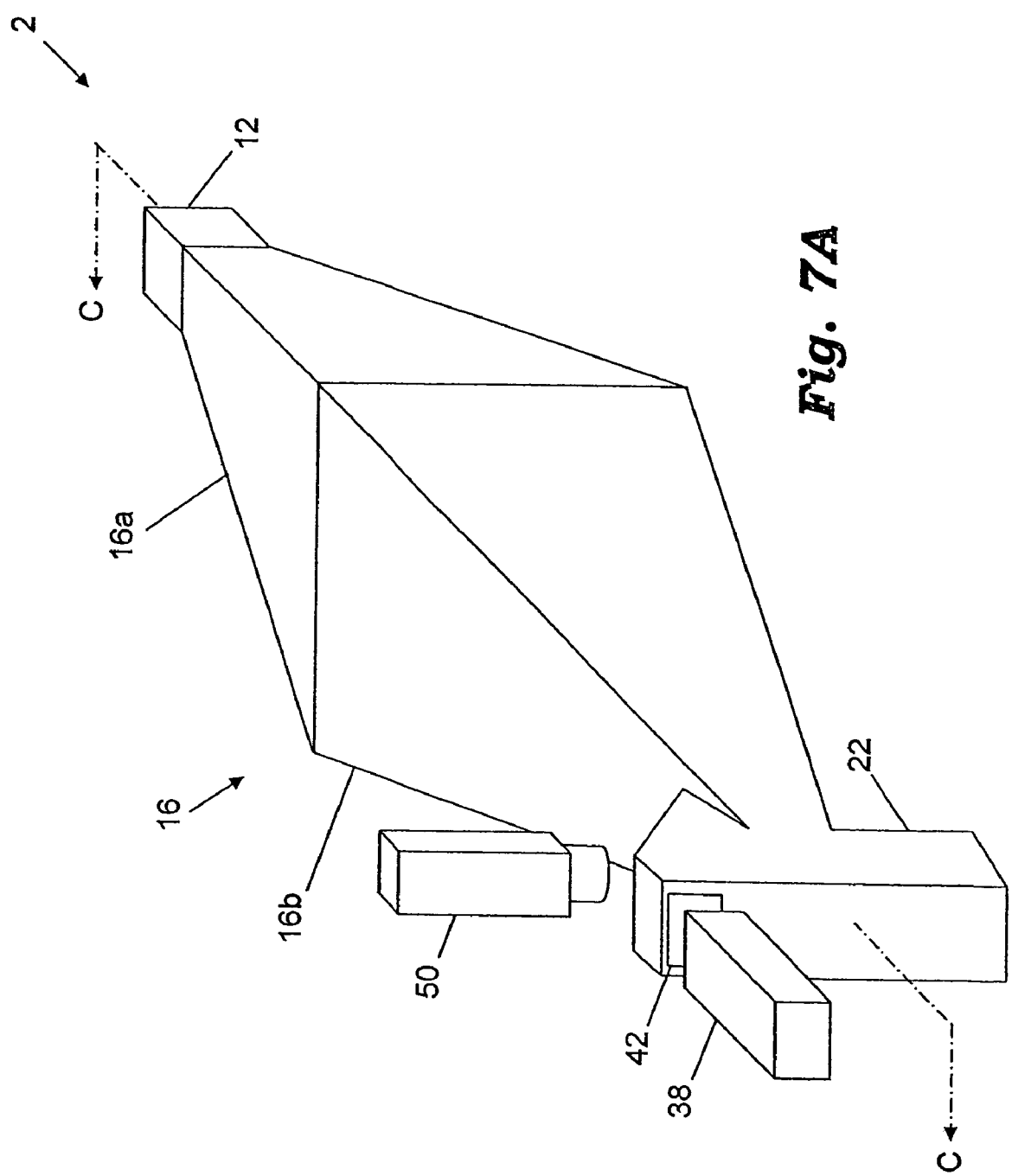

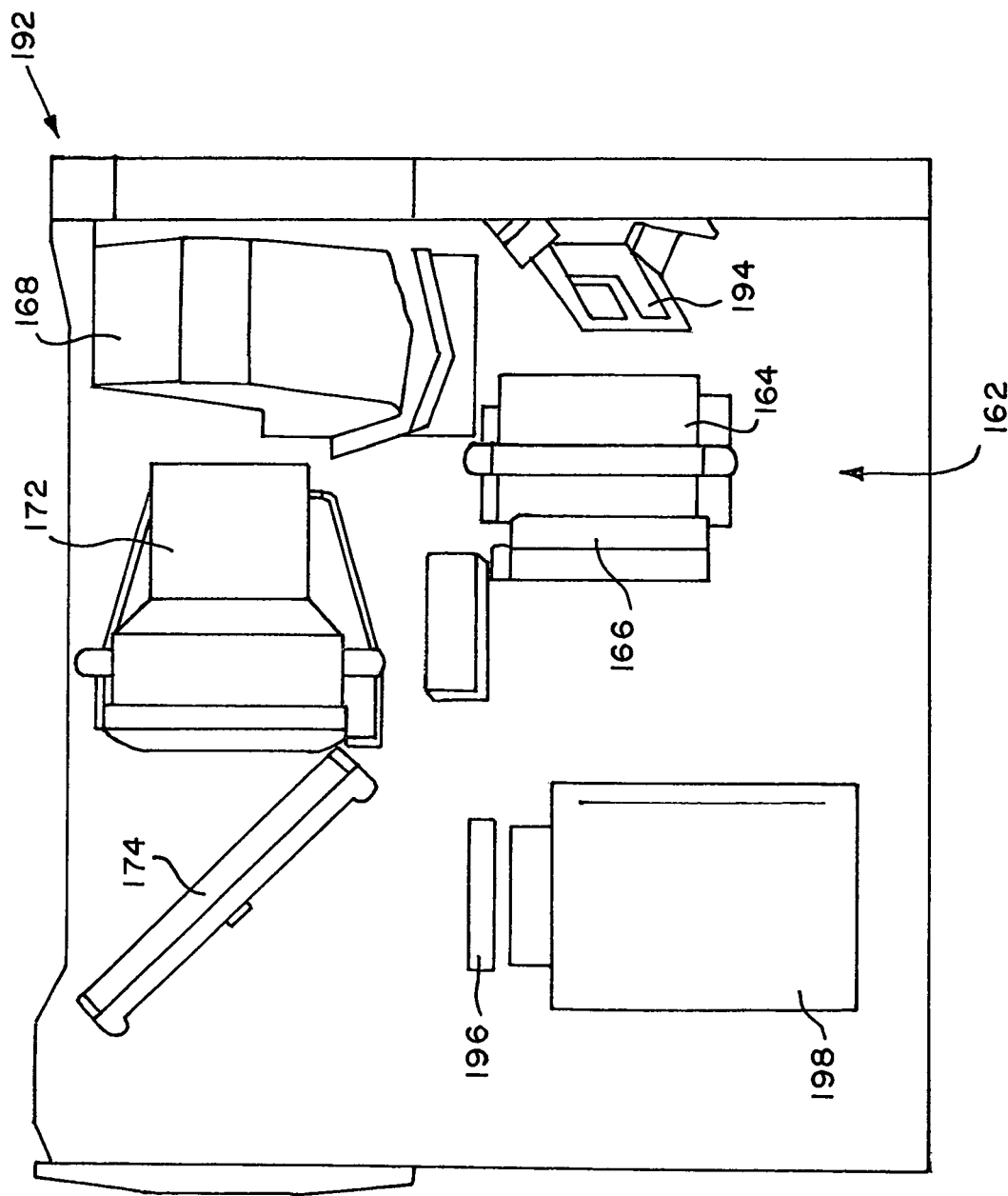
FIG.15
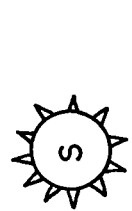
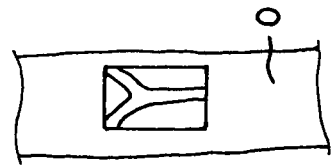
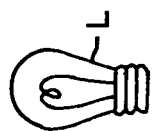

FIG. 16a

Artifact Removal Program

| | | |
|---|---|---|
| [0010] | cd, 'd:\data\vascular\hair\new' | ; go to the directory for the data file to process |
| [0020] | dummy = bytarr(15) | ; the array to hold the header information |
| [0030] | | ; in the image file |
| [0040] | result = bytarr(640,480) | ; the array to hold the image captured from |
| [0050] | | ; VeinViewer |
| [0060] | openr, 1, 'matt1.pgm' | ; open the image file |
| [0070] | readu, 1, dummy,result | ; read the header and image data |
| [0080] | close, 1 | ; close the image file |
| [0090] | | ; open an image window on the computer screen |
| [0100] | window, 0, xsize = 640, ysize = 480, xpos = 640, ypos = 0, title = 'original' | |
| [0110] | tv, result | ; display the image from the file |
| [0120] | im1 = float(result) / 255. | ; put the image in a floating point array |
| [0130] | | ; with pixel values between 0.0 and 1.0 |
| [0140] | | ; |
| [0150] | gi1 = gauss(im1, 640, 480, 8.) | ; smooth the image with a Gaussian convolution |
| [0160] | | ; with a sigma equal to 8.0 pixels |
| [0170] | di1 = im1 - gi1 | ; create a difference image which is the original |
| [0180] | | ; image minus the smoothed image |
| [0190] | ng1 = where(di1 lt 0.0) | ; find those pixels where the difference image |
| [0200] | | ; is negative |
| [0220] | im1(ng1) = gi1(ng1) | ; replace those pixels with the corresponding |
| [0230] | | ; pixels from the smoothed image |
| [0240] | mk1 = fltarr(640, 480) | ; create a new floating point array the size of |
| [0250] | | ; the image and set all pixels to 0.0 |
| [0260] | mk1(ng1) = 1.0 | ; set the pixels in the new array that correspond |
| [0270] | | ; to the negative pixels in the difference image |
| [0280] | | ; to 1.0 |
| [0290] | im2 = im1 + 0.015 * mk1 | ; add 0.015 times the new array to the image |
| [0300] | | ; |
| [0310] | gi2 = gauss(im2, 640, 480, 8.) | ; smooth the image with a Gaussian convolution |
| [0320] | | ; with a sigma equal to 8.0 pixels |
| [0330] | di2 = im2 - gi2 | ; create a difference image which is the original |
| [0340] | | ; image minus the smoothed image |
| [0350] | ng2 = where(di2 lt 0.0) | ; find those pixels where the difference image |
| [0360] | | ; is negative |
| [0370] | im2(ng2) = gi2(ng2) | ; replace those pixels with the corresponding |
| [0380] | | ; pixels from the smoothed image |
| [0390] | mk2 = fltarr(640, 480) | ; create a new floating point array the size of the |
| [0410] | | ; image and set all pixels to 0.0 |
| [0420] | mk2(ng2) = 1.0 | ; set the pixels in the new array that correspond |
| [0430] | | ; to the negative pixels in the difference image |
| [0440] | | ; to 1.0 |
| [0450] | im3 = im2 + 0.015 * mk2 | ; add 0.015 times the new array to the image |
| [0460] | | ; |
| [0470] | sm3 = gauss(im3, 640, 480, 64.) | ; smooth the image with a Gaussian convolution |
| [0480] | | ; with a sigma equal to 64.0 pixels |
| [0490] | di3 = im3 - sm3 | ; create a difference image which is the original |

FIG. 16b

[0500]                                                    ; image minus the smoothed image
[0510]   ai3 = abs(di3)                          ; create an image which is the absolute value of
[0520]                                                    ; the difference image
[0530]   ; smooth the absolute value image with a Gaussian convolution with a sigma
[0540]   ; equal to 64.0 pixels
[0550]   denom = gauss(ai3, 640, 480, 64.)
[0560]   edg = di3 / denom                    ; divide the difference image with the smoothed
[0570]                                                    ; absolute value image
[0580]   ged = gauss(edg, 640, 480, 4.)   ; smooth the divided image with a Gaussian
[0590]                                                    ; convolution with sigma equal to 4.0 pixels
[0600]   ;
[0610]   ; open an image window on the computer screen
[0620]   window, 1, xsize = 640, ysize = 480, xpos = 640, ypos = 515, title='processed'
[0630]   tvscl, ged                                 ; display the processed image
[0640]   end                                           ; end the program

FIG. 17a

Artifact Removal Program in C++ Programming Language

```
[1010]  // Process Image using Algorithm 1 (adaptive)
[1020]  void ProcessImage1(Ipp8u* pFirst, Ipp8u *pLast)
[1030]  {
[1040]     int adapfactor, adaprange;
[1050]     IppiSize mask, mask2;
[1060]     IppiPoint anchor, anchor2;
[1070]
[1080]     if (!child) {
[1090]        // FIRST kernel size. Used to blur the original image.
[1100]        kernelSize = 192;    // 128
[1110]        mask.width=mask.height=kernelSize;
[1120]        anchor.x=anchor.y=(int)(kernelSize/2);
[1130]
[1140]        // SECOND kernel size. Used in the adaptive part of the algorithm.
[1150]        kernelSize2 = 96;    // 64
[1160]        mask2.width=mask2.height=kernelSize2;
[1170]        anchor2.x=anchor2.y=(int)(mask2.width/2);
[1180]     } else {
[1190]        // FIRST kernel size. Used to blur the original image.
[1200]        kernelSize = 96;    // 96
[1210]        mask.width=mask.height=kernelSize;
[1220]        anchor.x=anchor.y=(int)(kernelSize/2);
[1230]
[1240]        // SECOND kernel size. Used in the adaptive part of the algorithm.
[1250]        kernelSize2 = 48;    // 48
[1260]        mask2.width=mask2.height=kernelSize2;
[1270]        anchor2.x=anchor2.y=(int)(mask2.width/2);
[1280]     }
```

FIG. 17b

```
[1290] ippiConvert_8u16s_C1R(pFirst, 640, pTwo, 640*2, roiVGA);
[1300] // converts from 8 bit unsigned (pFirst) to 16 bit signed (pTwo)
[1310]
[1320] ownBlur(pTwo, pThree, mask, anchor);        //pThree = blur(pTwo)
[1330]
[1340] ippiSub_16s_C1RSfs(pThree, 640*2, pTwo, 640*2, pFour, 640*2, roiVGA, 0);
[1350] // pFour = pTwo - pThree, the result is a signed image
[1360]
[1370] ippiMinMax_16s_C1R(pFour, 640*2, roiVGA, &min, &max);
[1380] // finds the range of pFour
[1390]
[1400] /***** pFive = scale_up(pFour) *****/
[1410] adaprange=(abs(min)>abs(max))?abs(min):abs(max);
[1420] if (adaprange!=0)
[1430]    adapfactor=(int)(32767/adaprange);
[1440] else
[1450]    adapfactor=32767;
[1460] ippiMulC_16s_C1RSfs(pFour, 640*2, (Ipp16s)adapfactor, pFive, 640*2,
[1470]                     roiVGA, 0);
[1480]
[1490] // obtains the higher byte of each pixel of pFive
[1500] // and puts it into the higher byte of pSix
[1510] ippiAndC_16u_C1R((Ipp16u*)(void*)pFive, 640*2, (Ipp16u)0xFF00,
[1520]                  (Ipp16u*)(void*)pSix, 640*2, roiVGA);
[1530]
[1540] ippiRShiftC_16s_C1R(pFive, 640*2, 7, pSeven, 640*2, roiVGA);
[1550] // pSeven=LSB(pFive)
[1560]
[1570] ippiAbs_16s_C1R(pSeven, 640*2, pEight, 640*2, roiVGA);
[1580]
```

FIG. 17c

```
[1590]    ownBlur(pEight, pNine, mask2, anchor2);
[1600]
[1610]    ippiOr_16u_C1R((Ipp16u*)(void*)pSix, 640*2,  (Ipp16u*)(void*)pNine,
[1620]              640*2, (Ipp16u*)(void*)pTen, 640*2, roiVGA);
[1630]
[1640]
[1650]    ippiLUT_16s_C1R(pTen, 640*2, pEleven, 640*2, roiVGA, pAdapValues,
[1660]              pAdapLevels, nAdapLevels);
[1670]
[1680]    ippiMinMax_16s_C1R(pEleven, 640*2, roiVGA, &min, &max);
[1690]    // finds the range
[1700]
[1710]    ippiLUT_16s_C1R(pEleven, 640*2, pTwelve, 640*2, roiVGA, pValues, pLevels,
[1720]              nLevels);
[1730]
[1740]    ippiConvert_16s8u_C1R(pTwelve, 640*2, pLast, 640, roiVGA);
[1750]
[1760]  }
[1770]  // Process Image using Algorithm 2 (hair)
[1780]  void ProcessImage2(Ipp8u* pFirst, Ipp8u *pLast)
[1790]  {
[1800]
[1810]    int adapfactor, adaprange;
[1820]    IppiSize filterSize, mask;
[1830]    IppiPoint filterAnchor, anchor;
[1840]
[1850]    ippiConvert_8u16s_C1R(pFirst, 640, pIm1, 640*2, roiVGA);
[1860]    //converts from 8 bit unsigned (pFirst) to 16 bit signed (pTwo)
[1870]
[1880]    filterSize.width=filterSize.height=param1;
[1890]    filterAnchor.x=filterAnchor.y=(int)(filterSize.width/2);
```

FIG. 17d

```
[1900]  ownBlur(pIm1, pGi1, filterSize, filterAnchor);
[1910]
[1920]  ippiSub_16s_C1RSfs(pGi1, 640*2, pIm1, 640*2, pDi1, 640*2, roiVGA, 0);
[1930]  //pDi1 = pIm1 - pGi1
[1940]
[1950]  ippiThreshold_LTValGTVal_16s_C1R(pDi1, 640*2, pNg1, 640*2, roiVGA, 0,
[1960]                                    255, 0, 0); // select those less than 0
[1970]
[1980]  ippiConvert_16s8u_C1R(pNg1, 640*2, pNeg1, 640, roiVGA);
[1990]
[2000]  ippiCopy_16s_C1RSfs(pGi1, 640*2, pIm1, 640*2, roiVGA, pNeg1, 640);
[2010]
[2020]  ippiSet_16s_C1R(0, pMk1, 640*2, roiVGA);
[2030]  ippiSet_16s_C1MR(255, pMk1, 640*2, roiVGA, pNeg1, 640);
[2040]
[2050]  ippiMulC_16s_C1RSfs(pMk1, 640*2, (Ipp16s) firstWeight, pAux1, 640*2,
[2060]                       roiVGA, 10);
[2070]
[2080]  ippiMulC_16s_C1RSfs(pIm1, 640*2, (Ipp16s)1000, pAux2, 640*2, roiVGA, 10);
[2090]
[2100]  ippiAdd_16s_C1RSfs(pAux1, 640*2, pAux2, 640*2, pIm2, 640*2, roiVGA, 0);
[2110]
[2120]  filterSize.width=filterSize.height=param2;
[2130]  filterAnchor.x=filterAnchor.y=(int)(filterSize.width/2);
[2140]  ownBlur(pIm2, pGi2, filterSize, filterAnchor);
[2150]
[2160]  ippiSub_16s_C1RSfs(pGi2, 640*2, pIm2, 640*2, pDi2, 640*2, roiVGA, 0);
[2170]  // pDi2 = pIm2 - pGi2
[2180]
```

FIG. 17e

```
[2190] ippiThreshold_LTValGTVal_16s_C1R(pDi2, 640*2, pNg2, 640*2, roiVGA, 0,
[2200]                                  255, 0, 0); // select those less than 0
[2210]
[2220] ippiConvert_16s8u_C1R(pNg2, 640*2, pNeg2, 640, roiVGA);
[2230]
[2240] ippiCopy_16s_C1MR(pGi2, 640*2, pIm2, 640*2, roiVGA, pNeg2, 640);
[2250]
[2260] ippiSet_16s_C1R(0, pMk2, 640*2, roiVGA);
[2270] ippiSet_16s_C1MR(255, pMk2, 640*2, roiVGA, pNeg2, 640);
[2280]
[2290] ippiMulC_16s_C1RSfs(pMk2, 640*2, (Ipp16s) lastWeight - 1*stepWeight,
[2300]                     pAux1, 640*2, roiVGA, 10);
[2310]
[2320] ippiMulC_16s_C1RSfs(pIm2, 640*2, (Ipp16s)1000, pAux2, 640*2, roiVGA, 10);
[2330]
[2340] ippiAdd_16s_C1RSfs(pAux1, 640*2, pAux2, 640*2, pIm3, 640*2, roiVGA, 0);
[2350]
[2360] filterSize.width=filterSize.height=param3;
[2370] filterAnchor.x=filterAnchor.y=(int)(filterSize.width/2);
[2380] ownBlur(pIm3, pSm3, filterSize, filterAnchor);
[2390]
[2400] ippiSub_16s_C1RSfs(pSm3, 640*2, pIm3, 640*2, pDi3, 640*2, roiVGA, 0);
[2410]
[2420] ippiMinMax_16s_C1R(pDi3, 640*2, roiVGA, &min, &max); // finds the range
[2430] adaprange=(abs(min)>abs(max))?abs(min):abs(max);
[2440] if (adaprange!=0)
[2450]     adapfactor=(int)(32767/adaprange);
[2460] else
[2470]     adapfactor=32767;
```

FIG. 17f

```
[2480]  ippiMulC_16s_C1RSfs(pDi3, 640*2, (Ipp16s)adapfactor, pAux3, 640*2,
[2490]                     roiVGA, 0);
[2500]  ippiAbs_16s_C1R(pAux3, 640*2, pAi3, 640*2, roiVGA);
[2510]
[2520]  mask.width=mask.height=param4;
[2530]  anchor.x=anchor.y=(int)(mask.width/2);
[2540]  ownBlur(pAi3, pDenom, mask, anchor);
[2550]
[2560]  ippiAndC_16u_C1R((Ipp16u*)(void*)pAux3, 640*2, (Ipp16u)0xFF00,
[2570]                   (Ipp16u*)(void*)pAux4, 640*2, roiVGA);
[2580]  ippiRShiftC_16s_C1R(pDenom, 640*2, 7, pAux5, 640*2, roiVGA);
[2590]
[2600]  ippiOr_16u_C1R((Ipp16u*)(void*)pAux4, 640*2, (Ipp16u*)(void*)pAux5,
[2610]                 640*2, (Ipp16u*)(void*)pAux6, 640*2, roiVGA);
[2620]
[2630]  ippiLUT_16s_C1R(pAux6, 640*2, pEdg, 640*2, roiVGA, pAdapValues,
[2640]                  pAdapLevels, nAdapLevels);
[2650]
[2660]  mask.width=mask.height=4;
[2670]  anchor.x=anchor.y=(int)(mask.width/2);
[2680]  ownBlur(pEdg, pGed, mask, anchor);
[2690]
[2700]  ippiMinMax_16s_C1R(pGed, 640*2, roiVGA, &min, &max); // finds the range
[2710]
[2720]  ippiLUT_16s_C1R(pGed, 640*2, pAux7, 640*2, roiVGA, pValues, pLevels,
[2730]                  nLevels);
[2740]  ippiConvert_16s8u_C1R(pAux7, 640*2, pLast, 640, roiVGA);
[2750]  }
```

FIG. 25a

> solve({X1=a*x1+b*y1+c+d*x1*y1, X2=a*x2+b*y2+c+d*x2*y2, X3=a*x3+b*y3+c+d*x3*y3, X4=a*x4+b*y4+c+d*x4*y4}, {a,b,c,d});

```
> solve({Y1=g*x1+h*y1+k+f*x1*y1, Y2=g*x2+h*y2+k+f*x2*y2, Y3=g*x3+h*y3+k+f*x3*y3, Y4=g*x4+h*y4+k+f*x4*y4},
{g,h,k,f});
{
```

```
/******************************************************************
                    alignSVGA.cpp  -  description
*******************************************************************/ include <ipp.h>
include <MyVariables.h>
#include <math.h>
#include <tools.h>
#include <stdio.h>

///////////////////////////////////////////////////////////////////
// AlignImageSVGA()
// Purpose:    Aligns a 800x600 8 bit image, using the bilinear transformation
//             The coefficients (coe) are calculated during alignment calibration.
//
// Parameters:
//     source: Input, pointer to a Ipp8u structure with the image to be aligned.
//     pLast:  Output, pointer to a Ipp8u structure with the aligned image.
//
// Note: pLast points to a previously allocated memory block using ippiMalloc
// void AlignImageSVGA(const Ipp8u *source, Ipp8u *pLast)
{
    ippiWarpBilinearBack_8u_C1R(source, roiVGA, 640, rectVGA, pLast, screen->pitch,
                                rectSVGA, coe, IPPI_INTER_NN);
}
```

PROJECTION OF SUBSURFACE STRUCTURE ONTO AN OBJECT'S SURFACE

CROSS REFERENCE TO RELATED APPLICATIONS

This application is a continuation-in-part, and claims priority benefit, of U.S. patent application Ser. No. 10/386,249 (filed Mar. 11, 2003) entitled Imaging System using Diffuse Infrared Light (hereby specifically incorporated by reference in its entirety), which issued as U.S. Pat. No. 7,239,909 on Jul. 3, 2007, which itself was a continuation-in-part, and claims priority benefit, of U.S. patent application Ser. No. 09/487,007 (filed Jan. 19, 2000) entitled Diffuse Infrared Light Imaging System, which issued as U.S. Pat. No. 6,556,858 on Apr. 29, 2003 (hereby specifically incorporated by reference in its entirety).

STATEMENT REGARDING FEDERALLY SPONSORED RESEARCH OR DEVELOPMENT

Not applicable.

REFERENCE TO COMPACT DISC(S)

Not applicable.

TECHNICAL FIELD

The present invention is generally directed to generation of diffuse infrared light. More particularly, the invention is directed to a system for illuminating an object with diffuse infrared light, producing a video image of buried structure beneath the surface of the object based on reflected infrared light, and then projecting an image of the buried structure onto the surface of the object.

BACKGROUND OF THE INVENTION

Some medical procedures and treatments require a medical practitioner to locate a blood vessel in a patient's arm or other appendage. This can be a difficult task, especially when the blood vessel is small and/or the vessel is under a significant deposit of subcutaneous fat or other tissue. The performance of previous imaging systems designed to aid in finding such blood vessels has been lacking.

Therefore, a system for enhancing the visual contrast between subcutaneous blood vessels and surrounding tissue is needed.

BRIEF SUMMARY OF THE INVENTION

The foregoing and other needs are met by an apparatus for providing diffuse light towards an object, such as a patient, to enhance visibility of subcutaneous blood vessels. In one embodiment, the apparatus includes an array of light-emitting sources. Each light-emitting source is operable to emit infrared light having a wavelength toward the object. A power source provides power to the array, and the array can emit infrared light when the power source is enabled. The apparatus further includes a diffusing structure having more than one diffusion stage. Each diffusion stage provides a level of diffusion to the infrared light emitted from the array as the emitted light passes through the diffusing structure.

In another embodiment, an apparatus is disclosed for providing diffuse light to an object. The apparatus includes an array of light-emitting sources, each source for emitting infrared light having a wavelength toward the object. A power source provides power to the array. The apparatus further includes diffusing structure which provides various levels of diffusion to the infrared light emitted from the array. The diffusing structure includes a first diffusing layer which is disposed adjacent to the array. The first diffusion layer provides a first level of diffusion to the light emitted by the array. A second diffusing layer is spaced apart from the first diffusing layer and provides a second level of diffusion to the light emitted by the array. A polarizer is included to polarize the light emitted by the array.

In yet another embodiment, an apparatus is disclosed which provides diffuse light to an object. The apparatus includes a light source for emitting infrared light toward the object. A first diffusing layer having a first diffusing plane intercepts light from the light source and provides a first amount of diffusion to the infrared light emitted by the light source. The apparatus includes a video imaging device for receiving light reflected from the object. The video imaging device operates to provide a video image of the object based on the reflected light.

In yet another embodiment, an apparatus is disclosed for providing diffuse light to an object. Groups of light-emitting diodes (LEDs) are arranged in a select pattern which define an LED plane. Each LED has an emitting surface for emitting infrared light towards the object and an electrical input for providing an electrical signal to the LED. The apparatus includes a control circuit which provides control signals to activate one or more LEDs in a select group of LEDs. A diffusing structure is positioned to intercept and diffuse the infrared light emitted from one or more of the LEDs.

Using the invention described herein, subcutaneous blood vessels that are difficult or impossible to see under white light or under non-diffuse infrared light can be easily seen in a video image, where the subcutaneous blood vessels appear as dark lines against a lighter background of surrounding flesh.

Additional embodiments are presented showing a variety of configurations of illumination sources, imaging devices for viewing the image of subsurface or buried structure beneath the surface of the illuminated object, and projectors for projecting a processed image back onto the surface of the object. Because of the present invention's departure from the prior art by projecting the image of the buried structure back onto the surface of the object (rather than onto a screen or monitor that is remote from the surface of the object), an observer using the present invention is not subject to the substantial parallax errors that otherwise occur with prior art devices if an observer were to view from off-axis. In other words, because the projection is onto the surface of the object with the present invention, rather than onto a screen remote from the surface of the object, the image stays in the same position on the surface of the object as the observer moves off-axis. An important feature of all embodiments is that the image of buried structure viewed by the imaging device should be substantially within a first spectrum outside a second spectrum of the image that is projected back onto the surface of the object, thereby causing the imaging device to be blind to the image that is projected back onto the surface of the object. The substantial non-overlap of the spectrum of the viewed image of the buried structure with the spectrum of the projected image of the buried structure effectively decouples the image processing of the buried structure's image from interference by the projected image. Because the projected image is in a second spectrum, such as the visible light spectrum, and the illumination of the object for the imaging device is in a first spectrum, such as the infrared spectrum, a substantial non-overlap of the two spectrums is maintained. In another herein-disclosed embodiment, rather than illuminating the object with light that is primarily in the first spectrum, the object can be illuminated by broad-spectrum ambient light, and a first-spectrum bandpass filter is placed in front of the imaging device to remove all spectral components outside the first spectrum, thereby causing the imaging device to only see the first-spectrum component of the broad-spectrum diffuse light reflected from the object. In the preferred embodiments of the invention when used in a medical application to observe subcutaneous blood vessels, the first spectrum will preferably be the infrared spectrum.

Two mechanisms are described for keeping the image of the buried structure, as seen by the imaging device, in focus with a proper lens-to-subject distance. A first embodiment of this mechanism uses a pair of laser pointers directed toward the object from different angles, such that the two laser pointers only converge to the same spot when the target is at the proper lens-to-subject distance from the imaging device. A second embodiment of this mechanism adds a recognizable pattern, such as a text border, to the projected image such that the projected recognizable pattern will only be in focus on the surface of the target object when the target is at the proper lens-to-subject distance from the projector, thereby causing the target to also be at the proper lens-to subject distance from the imaging device.

Image processing is disclosed that removes undesired small artifacts, such as surface hair and other features, from the viewed image of buried structure prior to projection onto the surface of the object.

A calibration procedure is described wherein the projector projects a green target pattern onto a fluorescent screen, which converts the projected green target pattern into deep red light that is visible by the infrared imaging device. A computer program records the position of the viewed pattern and calculates calibration coefficients to be used in a bi-linear transformation to correct magnification, rotation, and translation misalignment between the imaging device and the projector.

BRIEF DESCRIPTION OF THE DRAWINGS

Further advantages of the invention will become apparent by reference to the detailed description of preferred embodiments when considered in conjunction with the drawings, which are not to scale, wherein like reference characters designate like or similar elements throughout the several drawings as follows:

FIG. 6a is a perspective view of an imaging system using diffuse infrared light according to an alternative embodiment of the invention;

FIG. 6b is a cross-sectional view of the imaging system of FIG. 6a;

FIG. 7a is a perspective view of an imaging system using diffuse infrared light according to another embodiment of the invention;

FIG. 7b is a cross-sectional view of the imaging system of FIG. 7a;

FIG. 15 is an internal view of a fifth version of the imaging system of the present invention, which uses ambient lighting to illuminate the viewed object.

FIGS. 16a and 16b, taken together in sequence, are a program listing for artifact removal image processing of the received image.

FIGS. 17a, 17b, 17c, 17d, 17e, and 17f, taken together in sequence, are a program listing in the C++ programming language for artifact removal image processing of the received image.

FIG. 25a and FIG. 25b are computer listings showing the solution for bi-linear transformation coefficients of the calibration procedure for the imaging system of the present invention.

FIG. 26 is a program listing in the C++ programming language, which performs the run-time correction to the viewed image of the object using coefficients determined during the calibration procedure.

DETAILED DESCRIPTION OF THE INVENTION

Skin and some other body tissues reflect infrared light in the near-infrared range of about 700 to 900 nanometers, while blood absorbs radiation in this range. Thus, in video images of body tissue taken under infrared illumination, blood vessels appear as dark lines against a lighter background of surrounding flesh. However, due to the reflective nature of subcutaneous fat, blood vessels that are disposed below significant deposits of such fat can be difficult or impossible to see when illuminated by direct light, that is, light that arrives generally from a single direction.

The inventor has determined that when an area of body tissue having a significant deposit of subcutaneous fat is imaged in near-infrared range under illumination of highly diffuse infrared light, there is significantly higher contrast between the blood vessels and surrounding flesh than when the tissue is viewed under direct infrared illumination. Although the invention should not be limited by any particular theory of operation, it appears that most of the diffuse infrared light reflected by the subcutaneous fat is directed away from the viewing direction. Thus, when highly diffuse infrared light is used to illuminate the tissue, the desired visual contrast between the blood vessels and the surrounding flesh is maintained.

Figure 1:
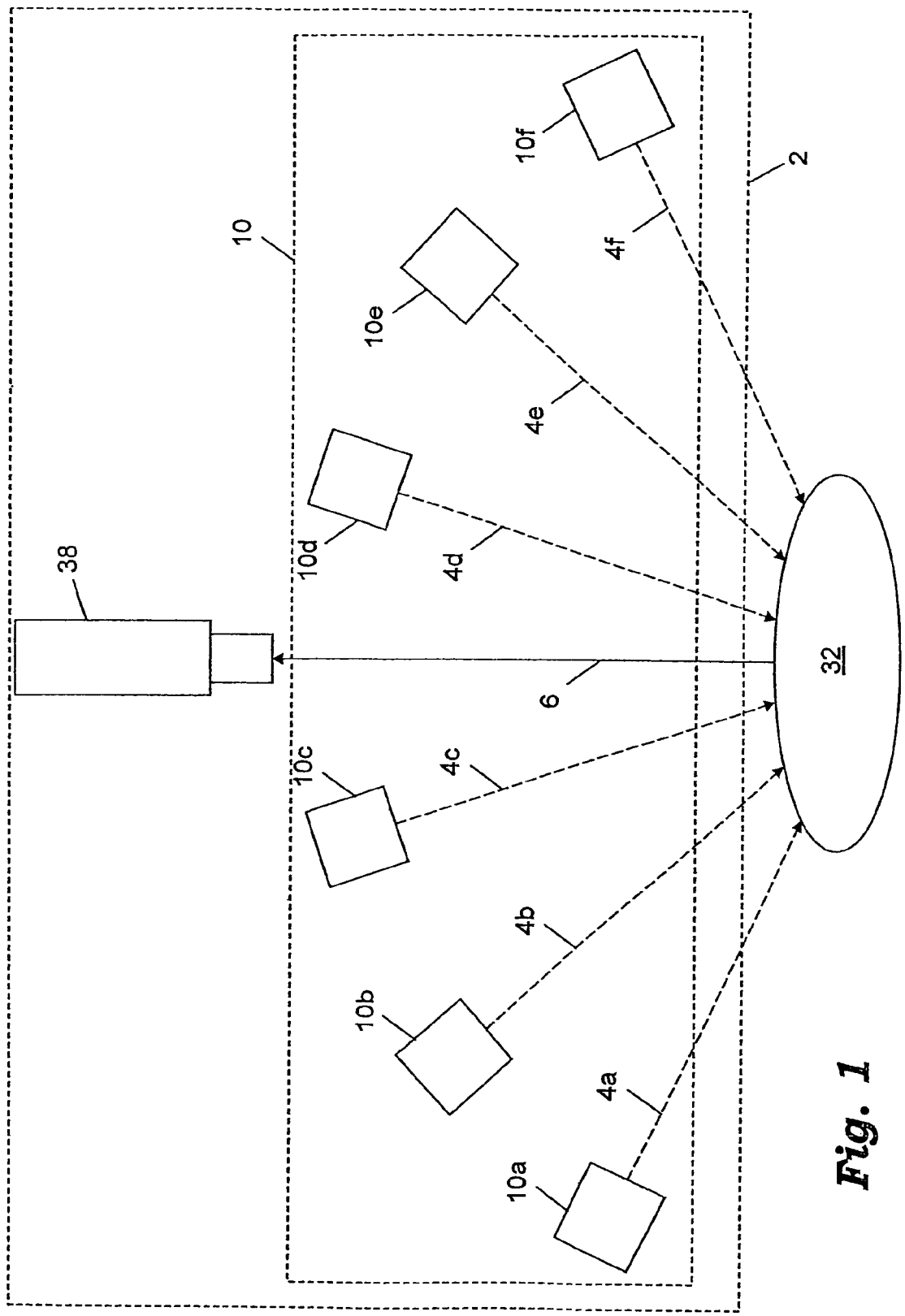
FIG. 1 depicts an imaging system for viewing an object under infrared illumination according to a preferred embodiment of the invention.

Shown in FIG. 1 is an imaging system 2 for illuminating an object 32, such as body tissue, with highly diffuse infrared light, and for producing a video image of the object 32 based upon infrared light reflected from the object 32. As described in detail herein, when the object 32 is body tissue, blood vessels that are disposed below subcutaneous fat in the tissue may be clearly seen in a video image produced by the system 2.

The imaging system 2 includes an illumination system 10 that illuminates the object 32 with infrared light from multiple different illumination directions. The system 10 includes multiple infrared light providers 10a-10f, each providing infrared light to the object 32 from a different illumination direction. The directions of arrival of the infrared light from each light provider 10a-10f are represented in FIG. 1 by the rays 4a-4f. As shown in FIG. 1, the directions of arrival of the infrared light ranges from perpendicular or near perpendicular to the surface of the object 32, to parallel or near parallel to the surface of the object 32. Since the infrared illumination arrives at the object 32 from such a wide range of illumination directions, the infrared illumination is highly diffuse.

As described in greater detail hereinafter, the light providers 10a-10f are preferably light reflecting surfaces that direct light from a single light source toward the object 32. In other embodiments, the light providers 10a-10f are individual light sources, or combinations of light sources and reflectors.

The imaging system 2 also includes an imaging device 38, such as a video camera, for viewing the object 32. The imaging device 38 views the object 32 from a viewing direction which is represented in FIG. 1 by the arrow 6. The imaging device 38 receives the diffuse infrared light reflected from the object 32, and generates an electronic video image of the object 32 based on the reflected infrared light.

Figure 2:
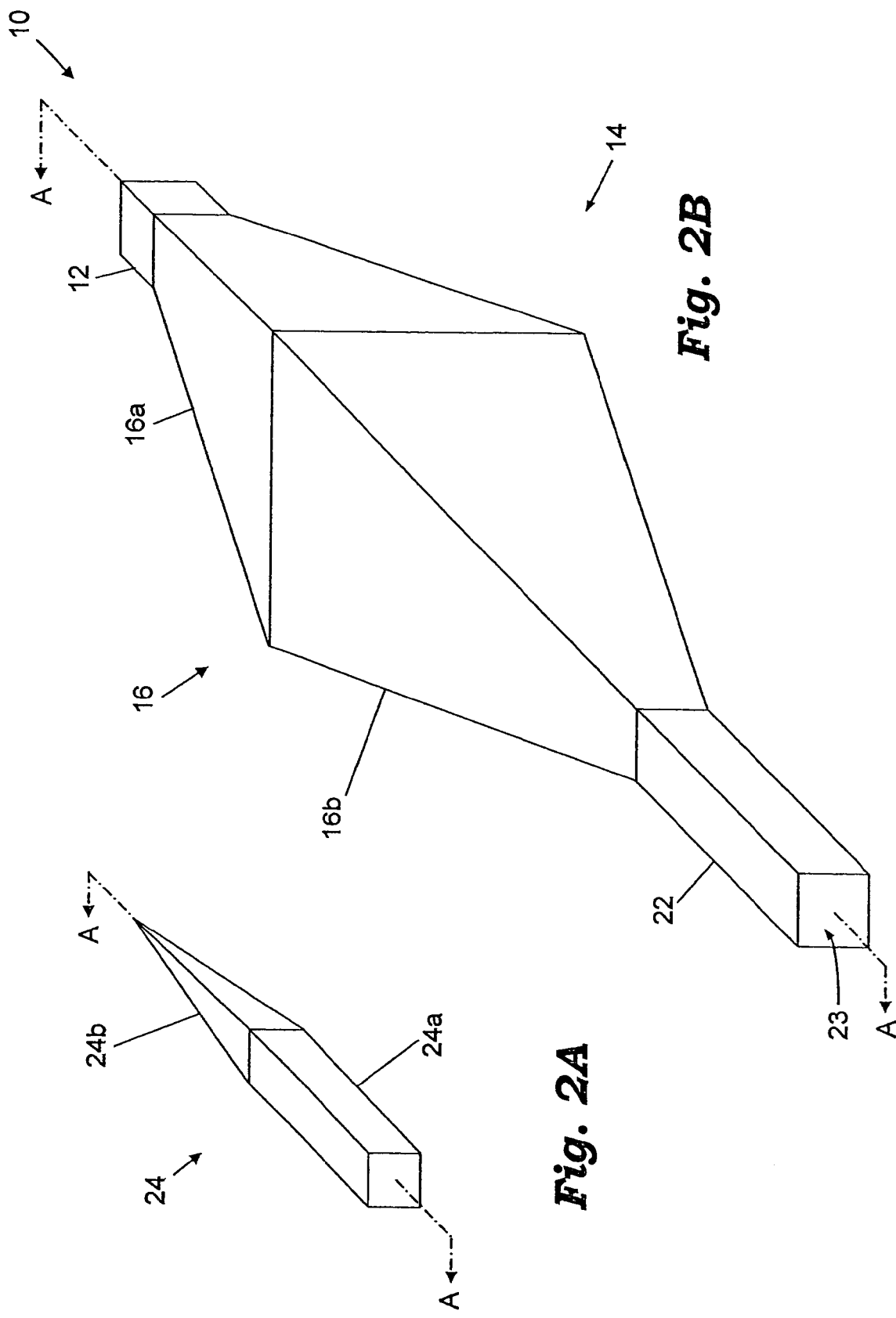
FIGS. 2a and 2b are perspective views of an imaging system using diffuse infrared light according to a preferred embodiment of the invention.
Figure 3:
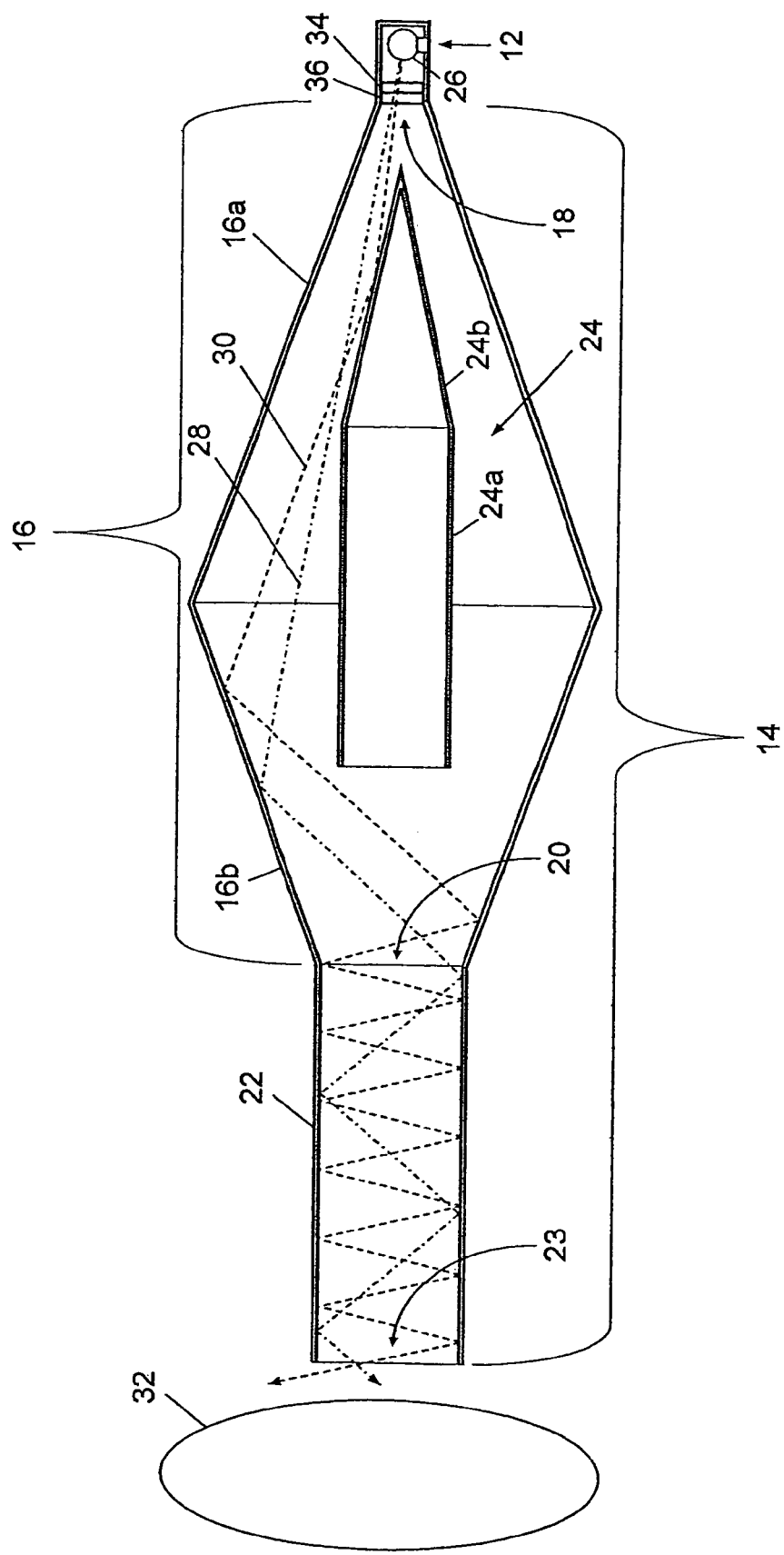
FIGS. 3 and 4 are cross-sectional views of the imaging system according to a preferred embodiment of the invention.

Shown in FIGS. 2a and 2b is a preferred embodiment of the illumination system 10. FIG. 3 depicts a cross-sectional view of the system 10 corresponding to the section A-A as shown in FIGS. 2a-b. The system 10 preferably includes a light source 12 that emits light into one end of a light diffusing structure 14. The light diffusing structure 14 includes an elongate outer enclosure 16 having reflective inner surfaces. Preferably, the inner surfaces of the elongate outer enclosure 16 are white in color. Alternatively, these reflective surfaces are mirrored surfaces, or a combination of white and mirrored surfaces. At the end of the light diffusing structure 14 opposite the light source 12, is a hollow light guide 22. As described in more detail below, the light guide 22 serves as an output aperture for the diffuse light.

The elongate outer enclosure 16 includes first and second sections 16a and 16b, each having a large end and a small end. Preferably, the first and second sections 16a and 16b are substantially pyramidal in shape, each having four trapezoidal faces. In the preferred embodiment, the four trapezoidal faces of the sections 16a and 16b are identical, such that each end of the sections 16a and 16b forms a square aperture. As shown in FIGS. 2a and 2b, the larger ends of the first and second sections 16a and 16b are joined together to form the enclosure 16.

At the small end of the first section 16a is an input aperture 18 formed by the four short sides of the four trapezoidal faces of the section 16a. The light source 12 is preferably attached to the small end of the first section 16a at the input aperture 18. Thus, the light generated by the light source 12 enters the elongate enclosure 16 at the input aperture 18, and illuminates the interior surfaces of the enclosure 16.

At the small end of the second section 16b is an output aperture 20 formed by the four short sides of the four trapezoidal faces of the section 16b. Attached at the output aperture 20 is one end of the hollow light guide 22. The light guide 22 preferably has white reflective inner surfaces similar to the inner surfaces of the enclosure 16.

The system 10 also includes an elongate inner reflector 24 which is disposed within and preferably coaxial with the outer enclosure 16. For clarity, the inner reflector 24 is shown in FIG. 2b removed from the outer enclosure 16. In the preferred embodiment, the inner reflector 24 is formed from a square tubular section 24a joined to the square base of a pyramidal section 24b. Preferably, the pyramidal section 24b has four sides that taper down to an apex. As shown in FIG. 3, the apex of the pyramidal section 24b is disposed proximate the input aperture 18 of the outer enclosure 16. The inner reflector 24 has reflective white outer surfaces similar to those of the inner surfaces of the outer enclosure 16.

The light diffusing characteristics of the structure 14 are best understood with reference to FIG. 3. Within the light source 12 is a lamp 26, such as a quartz-halogen bulb and gold-plated reflector manufactured by Gilway and having part number L517A-G. When energized, the lamp 26 produces electromagnetic radiation in the form of white light.

For purposes of this description, the lamp 26 may be thought of as a point source radiating light in multiple directions, as represented by the exemplary rays 28 and 30. As shown in FIG. 3, the ray 28 reflects from the inner surface of the section 16b of the outer enclosure 16. The ray 28 then travels through the output aperture 20, into the light guide 22, and, after multiple reflections from the inner surfaces of the light guide 22, emits from the exit aperture 23. The ray 30, which exits the light source 12 from a different angle than the ray 28, reflects from the inner reflector 24. The ray 30 then reflects from the inner surface of the section 16b of the outer enclosure 16, and travels through the output aperture 20 and into the light guide 22. After multiple reflections from the inner surfaces of the light guide 22, the ray 30 also emits from the exit aperture 23, but at a different angle than that of the ray 28.

When an object 32 is placed near the exit aperture 23, the rays 28 and 30 arrive at the object 32 from different angles. It will be appreciated that the light radiating from the light source 12 could be represented as an infinite number of rays which strike and reflect from the inner reflector 24 and the inner surfaces of the outer enclosure 16 from an infinite number of angles. Thus, the light emitted from the exit aperture 23 arrives at the object 32 from many different angles, and is therefore highly diffuse light. These arrival angles range from near perpendicular to near parallel with the plane of the exit aperture 23. Since the diffusing structure 14 is three-dimensional, it will be appreciated that light also reflects from the other surfaces of the outer enclosure 16 and the inner reflector 24, such as those that are perpendicular to the surfaces shown in FIG. 3. Therefore, the light emitted at the exit aperture 23 of the illumination system 10 is highly diffuse, appearing to be generated by many different light sources.

Due to the arrangement of the reflective inner surfaces of the outer enclosure 16 and the reflective outer surfaces of the inner reflector 24, the diffusing structure 14 efficiently transfers the light radiated from the lamp 26 to the exit aperture 23. Thus, a very large fraction of the light provided by the lamp 26 reaches the object 32, and very little light energy is wasted.

As described in more detail below, the illumination system 10 can be used to provide diffuse light for medical imaging purposes. However, it will be appreciated that the scope of the invention is not limited to medical uses. The system 10 could also be used as a diffuse light source for general photographic purposes.

In a preferred embodiment of the invention, as depicted in FIG. 3, the light source 12 includes a cold mirror 34 disposed between the lamp 26 and the input aperture 18 of the outer enclosure 16. The cold mirror 34 reflects substantially all light having wavelengths outside a selected infrared range of wavelengths. Preferably, the selected range includes wavelengths from approximately 700 to 1000 nanometers. Immediately proximate the cold mirror 34, and disposed between the cold mirror 34 and the input aperture 18, is an infrared transmitting filter 36 which further attenuates light having wavelengths outside the selected infrared range while transmitting light having wavelengths within the selected infrared range. Thus, the light that passes through the cold mirror 34 and the filter 36 into the outer enclosure 16 is infrared light having wavelengths within the selected infrared range.

It should be appreciated that there are other ways that the light source 12 could be configured to generate infrared light. For example, the light source 12 could consist of an infrared light-emitting diode (LED) or an array of infrared LEDs. Thus, the configuration of the light source 12 shown in FIG. 3 and described above is a preferred embodiment only, and the invention is not limited to any particular configuration of the light source 12.

Figure 4:
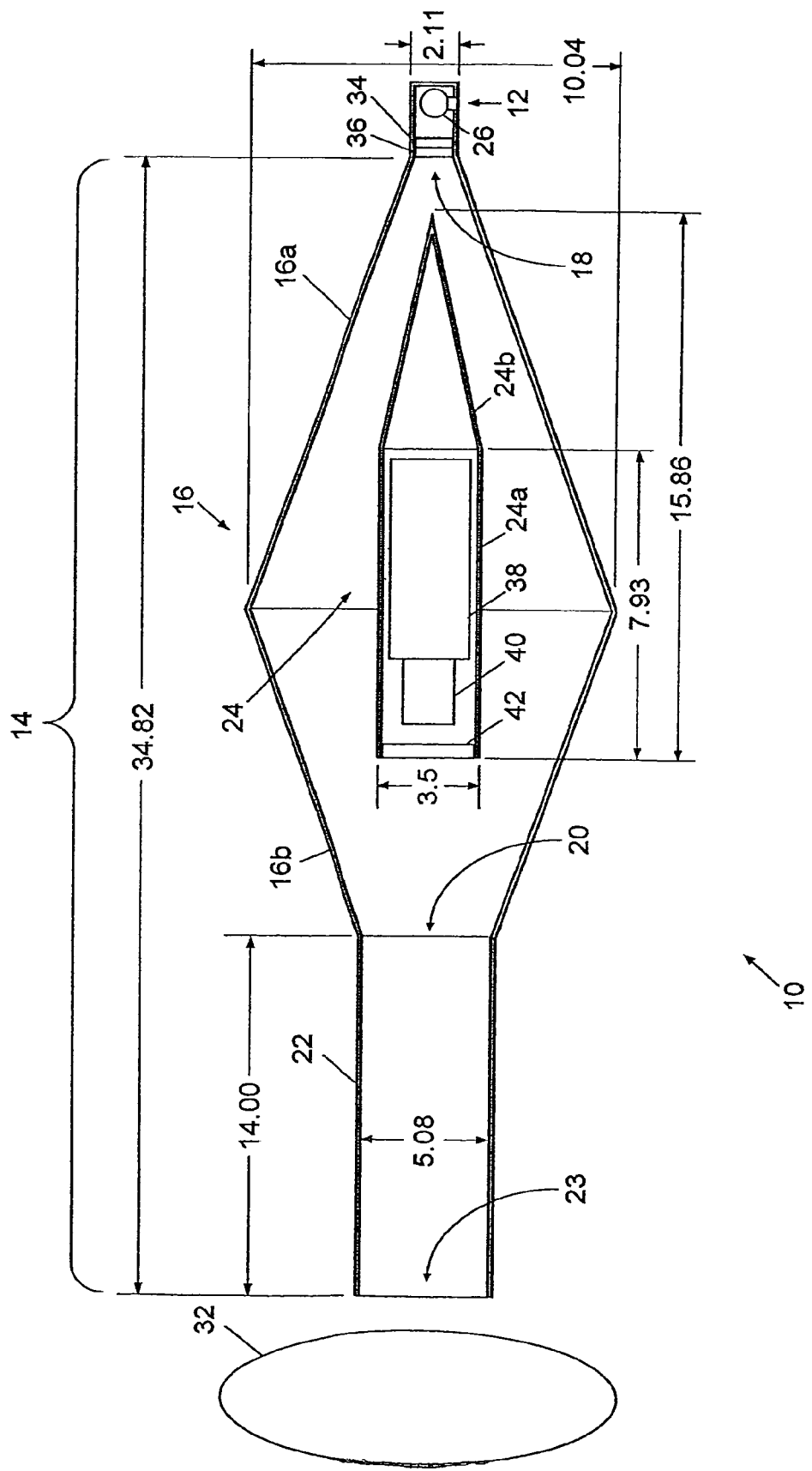

FIG. 4 depicts the dimensions of a preferred embodiment of the illumination system 10. As shown in FIG. 4, the total length of the light diffusing structure 14 is approximately 34.82 inches. The height and width of the outer enclosure 16 at the juncture of the first and second sections 16a and 16b is approximately 10.04 inches. The preferred length of the light guide 22 is approximately 14.00 inches, and its height and width is approximately 5.08 inches. Preferably, the total length of the inner reflector 24 is approximately 15.86 inches. The preferred length of the tubular section 24a of the inner reflector 24 is approximately 7.93 inches. The height and width of the tubular section 24a is approximately 3.5 inches. The height and width of the light source 12 is approximately 2.11 inches.

As shown in FIG. 4, a preferred embodiment of the invention includes a lens 40 used in conjunction with the video imaging device 38 to produce a video image of the object 32 based on diffuse light reflected from the object 32. Preferably, the imaging device 38 of this embodiment is a charge-coupled device (CCD) video camera 38 manufactured by Cohu, having model number 631520010000. The lens 40 of the preferred embodiment is a 25 mm f-0.95 movie camera lens manufactured by Angenieux.

The camera 38 and lens 40 of the preferred embodiment are disposed within the tubular section 24a of the inner reflector 24. As shown in FIG. 4, the open end of the tubular section 24a forms an aperture toward which the camera 38 and lens 40 are pointed. In this manner, the hollow light guide 22 is substantially centered within the field of view of the camera 38. Thus, the camera 38 receives light reflected from the object 32 that enters the light guide 22, travels through the enclosure 16, and enters the open end of the section 24a.

As shown in FIG. 4, the preferred embodiment of the invention includes an infrared-transmitting filter 42 disposed in the open end of the tubular section 24a. This filter 42 receives light reflected from the object 32, and any other light that may enter the enclosure 16, and substantially eliminates all light having wavelengths outside the infrared range of approximately 700 to 1000 nanometers. In the preferred embodiment, the filter 42 substantially eliminates light having wavelengths outside a selected infrared range of approximately 800 to 850 nanometers. Thus, the light that passes through the filter 42 and into the lens 40 is infrared light within the selected wavelength range. Therefore, the camera 38 primarily receives infrared light which originates from within the illumination system 10 and which is reflected from the object 32.

Figure 5:
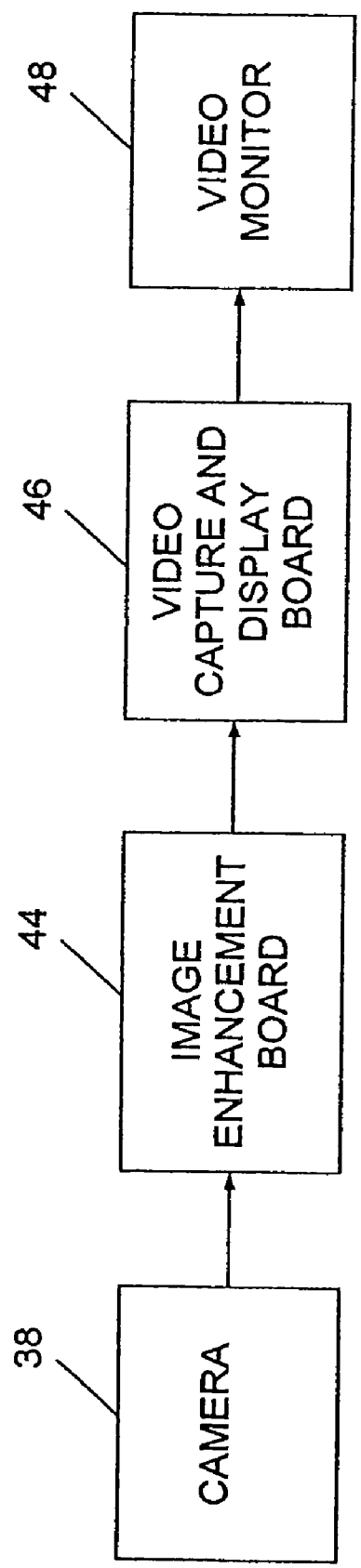
FIG. 5 is a functional block diagram of the imaging system according to a preferred embodiment of the invention.

Based on the light reflected from the object 32, the camera 38 generates a video image of the object 32 in the form of an electrical video signal. As shown in FIG. 5, the video signal is preferably provided to an image enhancement board 44, such as a board manufactured by DigiVision having a model number ICE-3000. The board 44 generates an enhanced video image signal based on the video signal from the camera 38. The enhanced video image signal is provided to a video capture and display card 46, such as a model 20-TD Live card manufactured by Miro. The card 46 captures still images from the image signal which may be saved in digital format on a digital storage device. The card 46 also formats the video image signal for real-time display on a video monitor 48.

It should be appreciated that the illumination system 10 could use other means for generating diffuse infrared light in accordance with the invention. For example, the light providers 10a-10f of FIG. 1 could be embodied by a ring-light strobe light. Alternatively, a circular array of LEDs could be used to illuminate a plastic transmitting diffuser placed near the surface of the object 32. In the latter embodiment, the light providers 10a-10f would correspond to the individual LEDs in the array.

In an alternative embodiment of the invention depicted in FIGS. 6a and 6b, the imaging system 2 includes a video projector 50 for illuminating the object 32 with an image of the object 32 to enhance the visual contrast between lighter and darker areas of the object 32. As described in U.S. Pat. No. 5,969,754, entitled CONTRAST ENHANCING ILLUMINATOR, the contents of which are incorporated herein by reference, the features of an object are visually enhanced for an observer when the features of a projected visible-light image of the object overlay the corresponding features of the object. The overlaid visible-light image causes the bright features of the object to appear brighter while the dark areas remain the same.

The embodiment of the invention shown in FIGS. 6a and 6b provides diffuse infrared light (represented by the rays 52) to the object 32 in a manner similar to that described previously. However, in the embodiment shown in FIGS. 6a and 6b, the optical path of the illuminating light is folded, such that the exit aperture 23 of the light guide 22 is rotated by 90 degrees relative to the exit aperture shown in FIGS. 1-3.

As shown in FIG. 6b, a beam separator, such as a hot mirror 54, receives infrared light 52 from the interior of the light diffusing structure 14 and reflects the infrared light 52 into the light guide 22 and toward the object 32. The hot mirror 54 also receives an infrared image of the object 32 (represented by the ray 56) and reflects it toward the camera 38. The hot mirror 54 receives the visible-light image (represented by the ray 58) from the projector 50 and transmits it into the light guide 22 and toward the object 32.

As explained in greater detail in U.S. Pat. No. 5,969,754, the video output signal from the video camera 38 is provided as a video input signal to the projector 50. Based on the video-input signal, the projector 50 projects the visible-light image 58 of the object 32 toward the hot mirror 54. The hot mirror 54 receives the visible-light image 58 and transmits it into the light guide 22 toward the object 32. By proper alignment of the projected visible-light image 58 from the projector 50 with the infrared image 56 of the object 32 which is sensed by the camera 38, the features in the projected visible-light image 58 are made to overlay the corresponding features of the object 32.

When the object 32 is body tissue, and the invention is used to find subcutaneous blood vessels in the body tissue, the blood vessels appear as dark lines in the projected visible-light image 58. Thus, when the visible-light image 58 is projected onto the body tissue, the subcutaneous blood vessels will lie directly beneath the dark lines in the projected visible-light image 58. In this manner, the invention significantly improves a medical practitioner's ability to find subcutaneous blood vessels while minimizing discomfort for the patient.

Figure 7B:
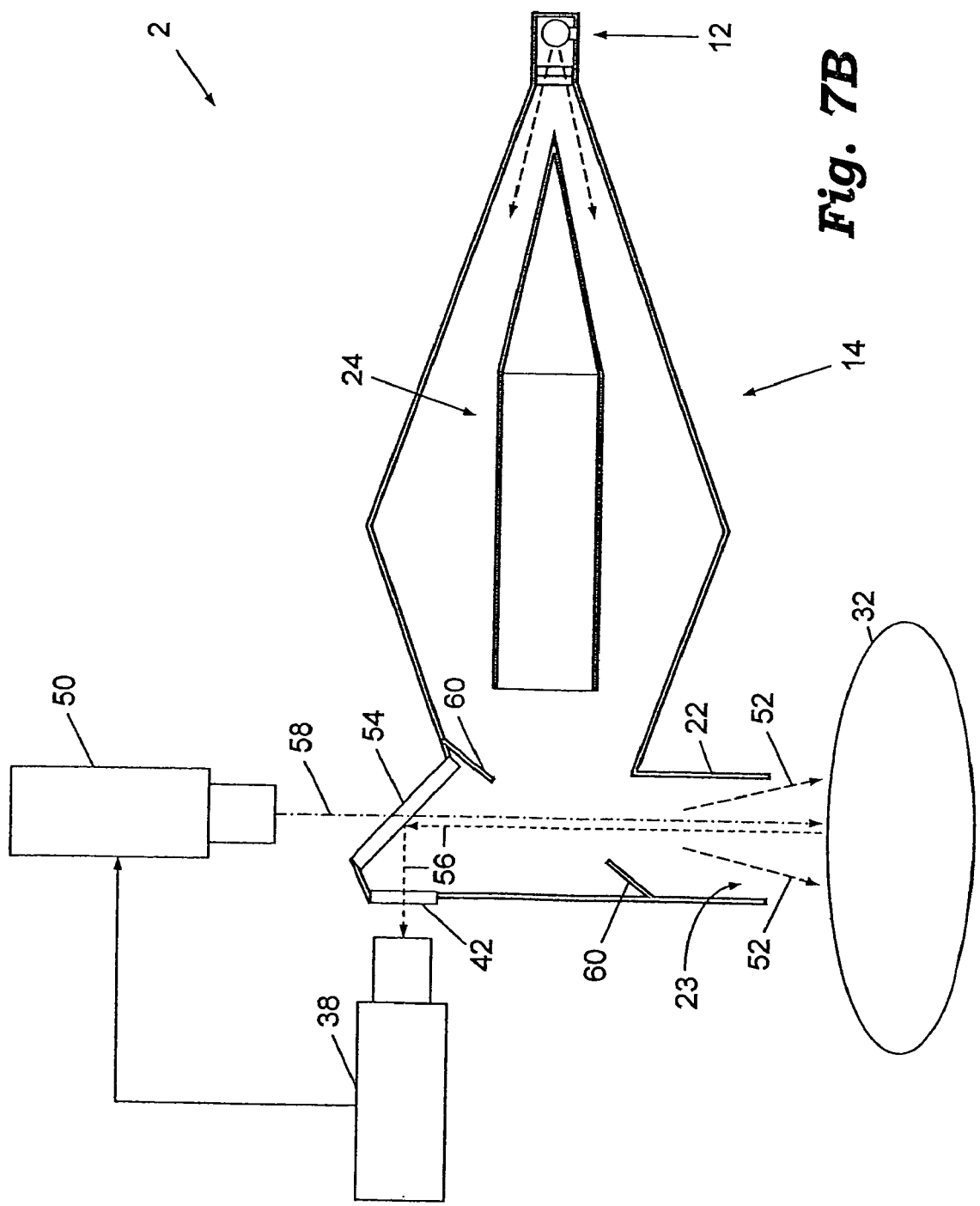

FIGS. 7a and 7b depict an alternative embodiment of the invention for use as a contrast enhancing illuminator. The embodiment of FIGS. 7a-b operates in a fashion similar to the embodiment of FIGS. 6a and 6b. However, in the embodiment of FIGS. 7a-b, the camera 38 is located outside the light diffusing structure 14. To accommodate the different location of the camera 38, the hot mirror 54 shown in FIGS. 7a-b is rotated by 90 degrees clockwise relative to its position in FIGS. 6a-b. Otherwise, the hot mirror 54 serves a similar function as that described above in reference to FIGS. 6a-b. Also to accommodate the different camera location, the infrared-transmitting filter 42 is mounted in a wall of the light guide 22. A reflective panel 60 is provided in this embodiment to further direct the light from the light source 12 into the light guide 22 and toward the exit aperture 23. Preferably, the panel 60 is a flat reflective sheet having an orifice therein to allow light to pass between the object 32 and the camera 38 and projector 50.

A preferred embodiment of a relatively compact and highly reliable imaging system 70 is depicted in FIGS. 8-11. The imaging system 70 is most preferably configured to illuminate an object 71, such as body tissue and the like, and to produce a video image of the object 71 based upon infrared light reflected from the object 71. The imaging system 70 preferably includes a housing 72 which contains the imaging features of the system 70.

Figure 8:
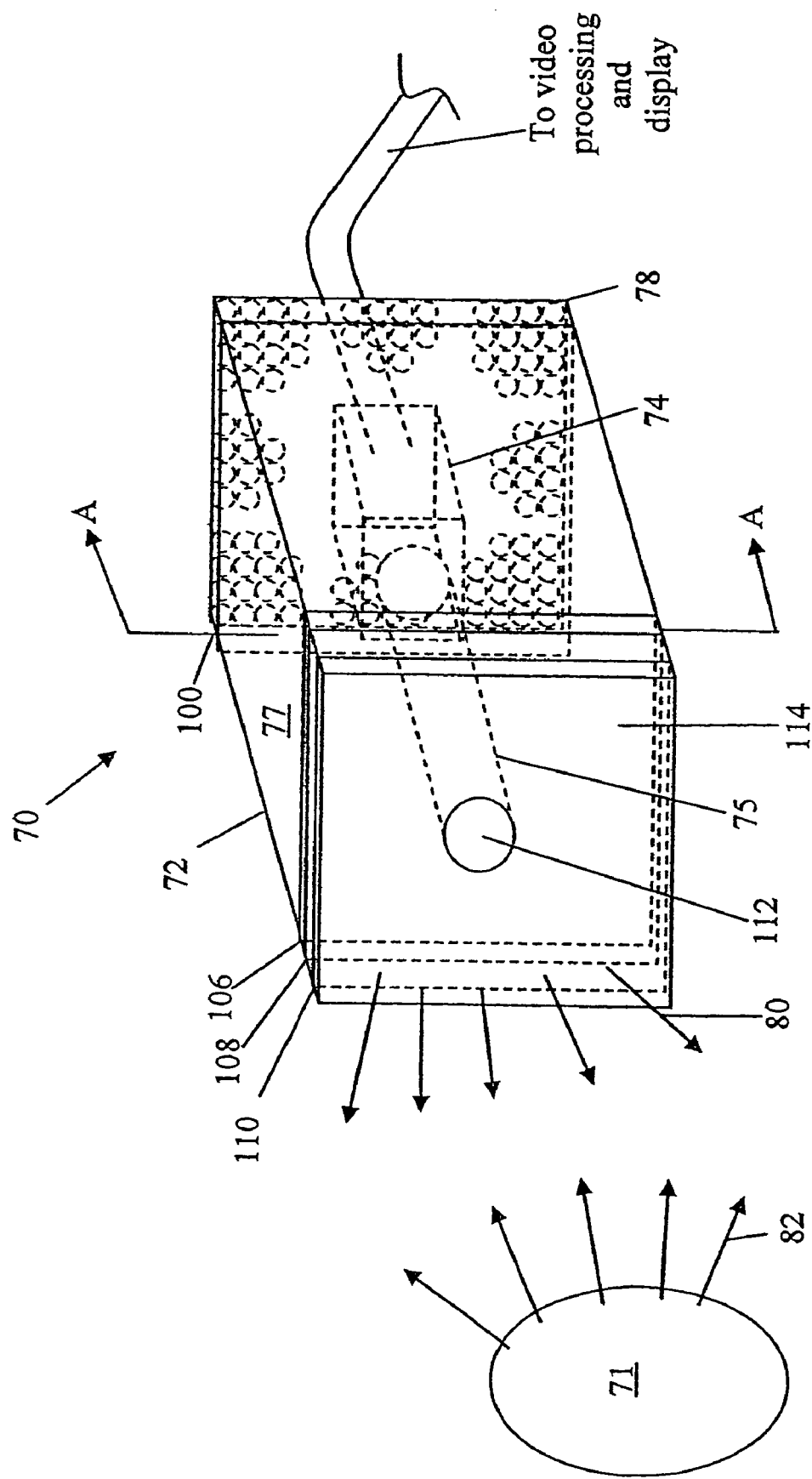
FIG. 8 is an isometric view of yet another aspect of an imaging system.

As shown in FIG. 8, the housing 72 preferably has a substantially rectangular configuration. The housing 72 preferably has a length of between about three and about five inches and a width of about three and one-half inches. It will be appreciated by those skilled in the art that the imaging system 70 can be configured in a variety of ways and the invention should not be limited by any specific examples or embodiments discussed herein. For example, in FIG. 8 the housing is depicted as being substantially rectangular, however, circular, polygonal, and other geometries and sizes are feasible as well.

Figure 9:
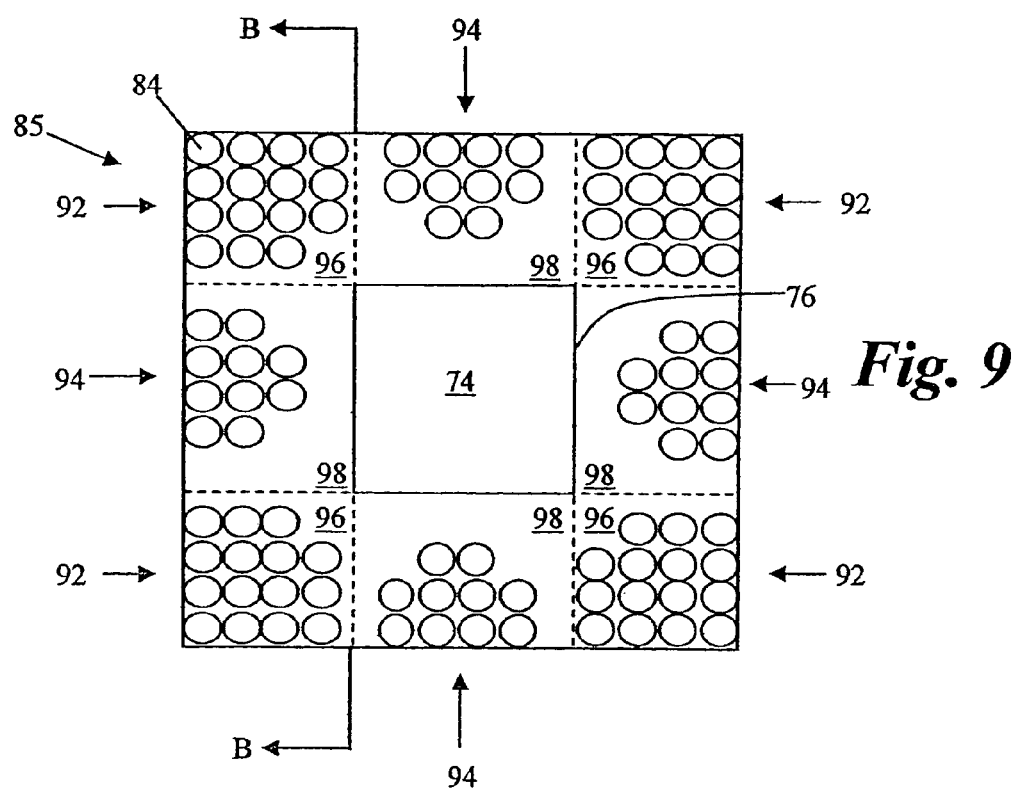
FIG. 9 is a front view of a portion of the imaging system as viewed in the direction of the arrows taken along line A-A of FIG. 8.

An imaging device 74, such as a video camera having a lens 75, and video processing components reside within the housing 72. The imaging device 74 and video processing components operate to detect infrared light and to process the detected infrared light from the object 71. The imaging system 74 produces an image based on the detected infrared light reflected from the object 71, as described herein. As shown in FIGS. 8 and 9, the imaging device 74 is preferably mounted within an aperture 76 of mounting wall 78, with the lens 75 extending into the housing interior 77, as described further below. More particularly, the camera 74 is preferably centrally and symmetrically mounted within the housing 72. This preferred symmetrical camera location tends to maximize the amount of light detected by the camera, which enhances the image produced by the system 70, thereby enhancing the illumination of blood vessels disposed below subcutaneous fat in body tissue.

The housing 72 most preferably contains various components operable to transmit diffuse light from the system 70 toward the object 71. Arrows 80 represent diffuse light transmitted by the system 70. Arrows 82 represent the light reflected from the object 71. As shown in FIG. 9, as viewed in the direction of the arrows along the section line A-A of FIG. 8, the wall 78 contains a number of infrared light emitting diodes (LEDs) 84 disposed in a LED array 85 for emitting infrared light. The LED array 85 defines a LED plane of reference. When activated, each LED 84 preferably transmits light at a wavelength of about 740 nanometers (nm). In the preferred embodiment, each LED 84 is manufactured by Roithner Lasertechnik of Austria under model number ELD-740-524.

Figure 10:
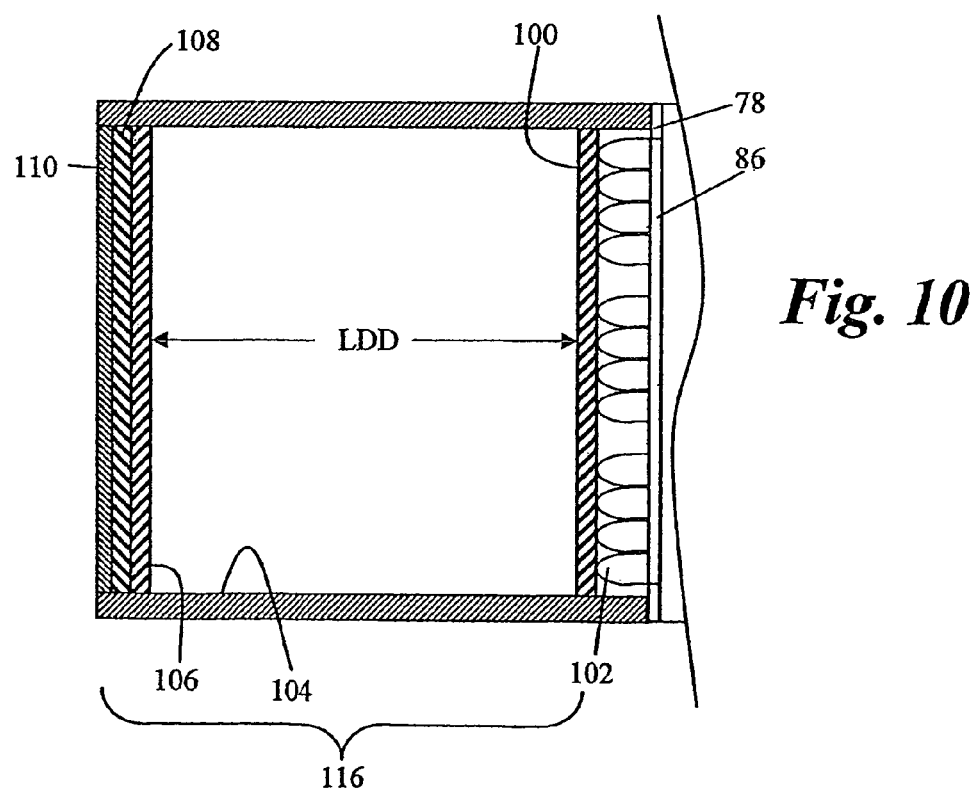
FIG. 10 is a cross-sectional side view taken along line B-B of FIG. 9.

As shown in FIG. 10, and according to the preferred embodiment, the LEDs 84 are mounted on a circuit board 86 located adjacent to wall 78. As shown in FIG. 9, there are most preferably eight groups 92, 94 of LEDs 84 concentrically arranged about the imaging system 74. The concentric LED arrangement tends to provide maximal dispersion and transmission of diffuse light from the system 70. It is preferred that each group 92, 94 of LEDs 84 contain at least ten LEDs 84. However, the system 70 can include more or fewer LEDs within a particular group depending upon a desired implementation of the system 70. Furthermore, the system 70 can include more or fewer groups of LEDs in the LED array 85.

With continuing reference to FIG. 9, there are four groups 92 of LEDs 84 located about the corner regions 96 of the LED array 85. Most preferably, at least fifteen LEDs 84 are disposed in each corner region 96 of the LED array 85. There are preferably four groups 94 of LEDs 84 disposed in lateral regions 98 of the LED array 85. Each lateral region 98 is located substantially between each corner region 94. Most preferably, at least ten LEDs 84 are disposed in each lateral region 98 of the LED array 85.

As described above, the LED array 85 is most preferably disposed on circuit board 86. In conjunction with the control system 90, the circuit board 86 includes control circuitry that controls the activation of one or more LEDs 84 within a particular group or groups 92, 94 of LEDs 84 in the LED array 85. As shown in the block diagram of FIG. 11, a power source 88 and a control system 90, such as a microprocessor or similar control device, are electrically connected to the circuit board 86. It will be appreciated that is also possible to control the LEDs without using a control system 90, that is, power source 88 can be switched "on" or "off" to activate and deactivate the LED array 85. It will be appreciated that pulse modulation techniques can also be used in conjunction with power source 88 to activate and deactivate one or more of the LEDs 84 in the LED array 85 according to a preferred duty cycle, herein defined as the LED "on" time relative to the LED "off" time.

Figure 11:
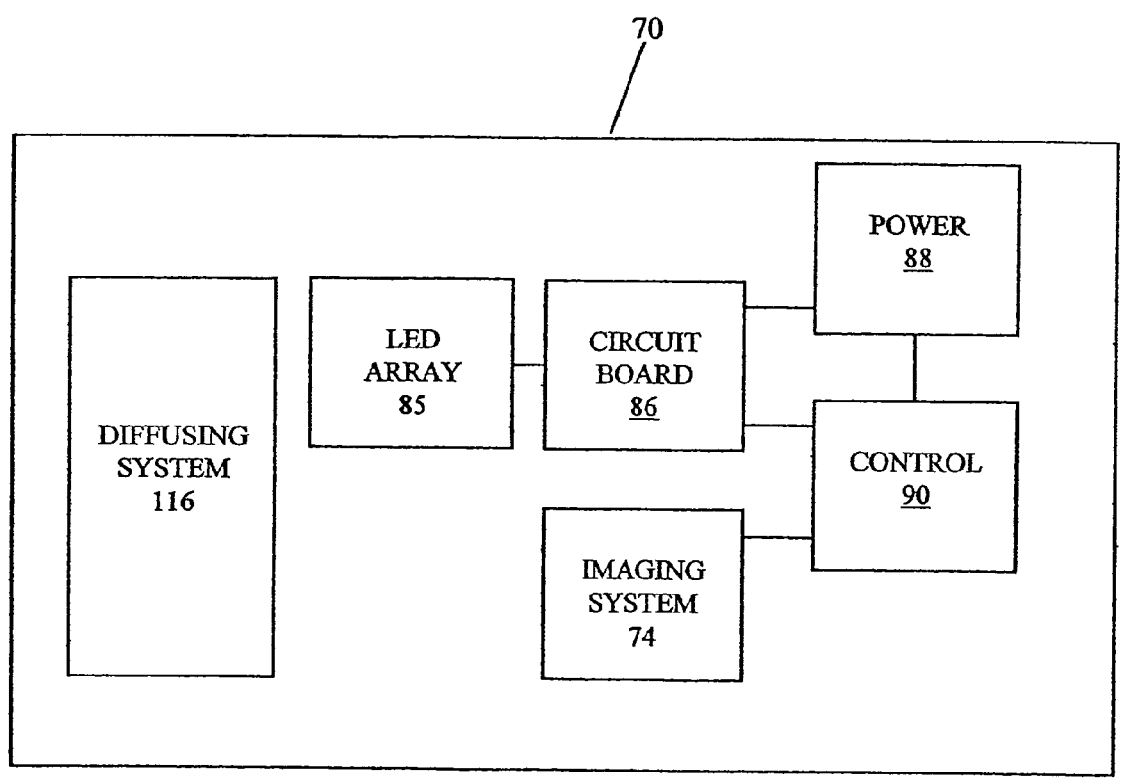
FIG. 11 is a block diagram of an imaging system.

As shown in the block diagram of FIG. 11, in a preferred embodiment of the imaging system 70, the LED array 85 is electrically connected via circuit board 86 to the power source 88 and control system 90. The control system 90 includes control features for controlling the LED array 85 to emit infrared light toward an object 71. As described herein, the control system 90 can enable one or more of the LEDs 84 in a group or groups of the LED array 85 to emit light continuously or intermittently. That is, one LED 84 or a plurality of LEDs 84 can be selected and controlled to emit infrared light intermittently or continuously toward the object 71. Thus, the system 70 can be configured to transmit infrared light from the LED array in various permutations and combinations of LEDs 84 and/or LED groups 92, 94.

Referring now to FIG. 10, a first diffusion layer 100 is disposed adjacent to the emitting surfaces 102 of the LEDs 84 in the LED array 85. According to a preferred embodiment, the first diffusion layer 100 is glued, such as using known adhesives, onto the emitting surfaces 102 of the LED array 85, thereby operating to diffuse the light emitted by one or more LEDs 84 in the LED array 85. The first diffusion layer 100 is most preferably a holographic twenty degree diffuser, such as a product having identification code LSD20PC10-F10×10/PSA, manufactured by Physical Optics Corporation of Torrance, Calif. Most preferably, the first diffusion layer 100 has a length of about three and one-half inches, a width of about three and one-half inches, and a thickness of about 0.10 inches. When one or more of the LEDs 84 in the LED array 85 are activated, the first diffusion layer 100 diffuses the infrared light emitted from the LED array 85, thereby providing a first amount of diffusion to the emitted infrared light.

The interior surfaces 104 of the housing 72 are shown in FIG. 10. Most preferably, the interior surfaces 104 are coated with a reflective coating, such as white paint or the like, which reflects and further diffuses the already diffuse light produced by the first diffusion layer 100. With continuing reference to FIG. 10, a second diffusion layer 106 is spaced apart from the first diffusion layer 100 by a distance LDD. Most preferably, the distance LDD between the first and second diffusion layers 100 and 106 is about three inches. The second diffusion layer 106 is most preferably a holographic twenty degree diffuser, similar to or the same as the above-described first diffusion layer 100. The second diffusion layer 106 has a preferred length of about three and one-half inches, a width of about three and one-half inches, and a thickness of about 0.10 inches.

The second diffusion layer 106 further diffuses the already diffuse light reflected from the interior surfaces 104 and provided by the first diffusion layer 100. As shown in FIG. 8, the first and second diffusion layers are substantially planar, that is, the layers 100 and 106 each define a planar geometry. According to the most preferred embodiment, the planes defined by the first and second diffusion layers 100 and 106 are substantially parallel with respect to one another. The preferred parallel planar arrangement of the diffusion layers 100, 106 tends to promote a quantifiable and uniform amount of diffuse light emanating from the system 70 when one or more of the LEDs 84 are enabled.

With continuing reference to FIG. 10, a backing material 108, such as LUCITE material sold under the trademark LUCITE and manufactured by DuPont of Wilmington, Del., is disposed adjacent to the second diffusion layer 106. Most preferably, the backing material has a thickness of about 0.125 inches. A visible polarizer 110 is disposed adjacent to the backing material 108. The visible polarizer 110 is most preferably manufactured by Visual Pursuits of Vernon Hills, Ill., under part number VP-GS-12U, and having a thickness of about 0.075 inches.

Thus, the system 70 is operable to produce various levels of diffusion as the emitted light progresses through the first diffusion layer 100, reflects off of the interior surfaces 104 of the first compartment 72a, and continues to progress through the second diffusion layer 106, backing material 108, and polarizer 110. Thus, a level of diffusion results after the emitted light passes through the first diffusion layer 100. Another level of diffusion results from the reflection from the interior surfaces 104 of the first compartment 72a of the already diffused light provided by the first diffusion layer 100. Yet another level of diffusion results after the diffuse light passes through the second diffusion layer 106.

As shown in FIG. 8, the visible polarizer 110 preferably includes a central portion 112, most preferably in the shape of a circle having about a one-inch diameter. The central portion 112 geometry most preferably coincides with the shape and dimension of the camera lens 75. The polarization of the central portion 112 is preferably rotated approximately ninety degrees with respect to the polarization of the surrounding area 114 of the polarizer 110. In the preferred embodiment, the camera lens 75 contacts the backing material 108. As shown in FIG. 8, the positional location of the lens 75 within the housing 70 preferably coincides with or shares the same central axis as the central portion 112 of the polarizer 110. The central portion 112 of the polarizer 110 coinciding with the front of the lens 75 tends to remove any surface glare ("specular reflection") in the resulting camera image.

As shown in FIG. 10, the backing material 108 and the visible polarizer 110 have planar surfaces which preferably include a similar planar orientation with respect to the planes defined by the first and second diffusion layers 100, 106. According to a most preferred embodiment, the first diffusion layer 100, interior surfaces 104, second diffusion layer 106, backing material 108, and visible polarizer 110 define a diffusing system 116 (FIG. 10) for providing diffuse light to an object 71. It will be appreciated that the diffusing structure can include more or fewer components and the invention is not to be limited by any specific examples or embodiments disclosed herein. For example, the diffusing system 116 can include either the first or the second diffusion layers 100, 106, with or without the polarizer 110, or can include the first and second diffusion layers 100, 106 without the polarizer 110.

Once actuated, the system 70 operates to transmit diffuse light 80 toward an object 71 and produce a video image of the object 71 with the imaging system 74, as described above. More particularly, once the power source 88 is enabled, one or more of the LEDs 84 in the LED array 85 emit infrared light from the emitting surface(s) 102. The first diffusion layer 100 provides a first amount of diffusion to the emitted infrared light. The interior surfaces 104 further diffuse the diffuse light emanating from the first diffusion layer 100. The second diffusion layer 106 further diffuses the already diffuse light which is then transmitted through the backing material 108 and the polarizer before illuminating the object 71. As described above, the object 71 reflects the emitted diffuse light 80 producing diffuse reflected light 82 that is captured by the imaging system 74. The imaging system 74 then produces a video image of the object 71. Accordingly, by emitting diffuse light according to a unique diffusion providing system 70, the system 70 aids in locating and differentiating between different material properties of the object 71, such as between blood vessels and tissue.

It is contemplated, and will be apparent to those skilled in the art from the preceding description and the accompanying drawings, that modifications and/or changes may be made in the embodiments of the invention. For example, the planes defined by the first or second diffusing layers 100 and 106 can be adjusted to not be parallel with respect to one another, thereby providing different levels of diffuse light from the system 70. Furthermore, the plane defined by the LED array 85 is most preferably in substantial parallel relation with respect to the plane defined by the first diffusing layer 100. However, the planes defined by LED array 85 and the first diffusing layer 100 can be varied to accommodate various operational conditions, as will be appreciated by those skilled in the art. Accordingly, it is expressly intended that the foregoing description and the accompanying drawings are illustrative of preferred embodiments only, not limiting thereto, and that the true spirit and scope of the present invention be determined by reference to the appended claims.

Figure 20A:
FIGS. 20a, 20b, and 20c are photographs of a processed image of subcutaneous blood vessels projected onto body tissue that covers the blood vessels.
Figure 20B:
Figure 20C:
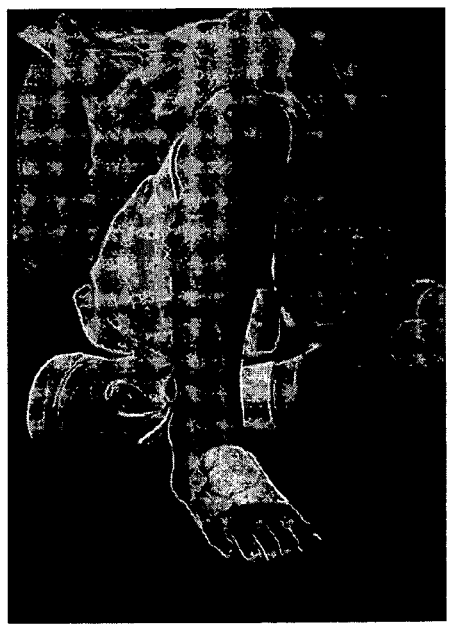

FIGS. 20a, 20b, and 20c are photographs of test subjects showing processed images of subcutaneous blood vessels being projected onto the surface of each subject's body tissue which covers the viewed blood vessels.

Additional embodiments will now be described showing a variety of configurations of illumination sources, imaging devices for viewing the image of buried structure beneath the surface of the illuminated object, and projectors for projecting the processed image back onto the surface of the object. Because all of the embodiments of the present invention have many structural features in common, only the differences between the structures need be discussed in detail, it being understood that similar structural features of all the embodiments perform similar functions. Those skilled in the art will readily recognize the similar structural features that appear in all embodiments of the present invention.

Because of the present invention's departure from the prior art by projecting the image of the buried structure back onto the surface of the object (rather than onto a screen or monitor that is remote from the surface of the object), an observer using the present invention is not subject to the parallax errors that otherwise occur with prior art devices if an observer were to view from off-axis. An important feature of all embodiments is that the image of buried structure viewed by the imaging device should be substantially within a first spectrum outside a second spectrum of the image that is projected back onto the surface of the object, thereby causing the imaging device to be blind to the image that is projected back onto the surface of the object. The substantial non-overlap of the spectrum of the viewed image of the buried structure with the spectrum of the projected image of the buried structure effectively decouples the image processing of the buried structure's image from interference by the projected image. Because the projected image is in the visible light spectrum and the illumination of the object for the imaging device is in the infrared spectrum, a substantial non-overlap of the two spectrums is maintained. In another herein-disclosed embodiment, rather than illuminating the object with light that is primarily in the infrared spectrum, the object can be illuminated by broad-spectrum ambient light, and an infrared filter is placed in front of the imaging device to remove all spectral components outside the infrared spectrum, thereby causing the imaging device to only see the infrared component of the broad-spectrum diffuse light reflected from the object.

Figure 12:
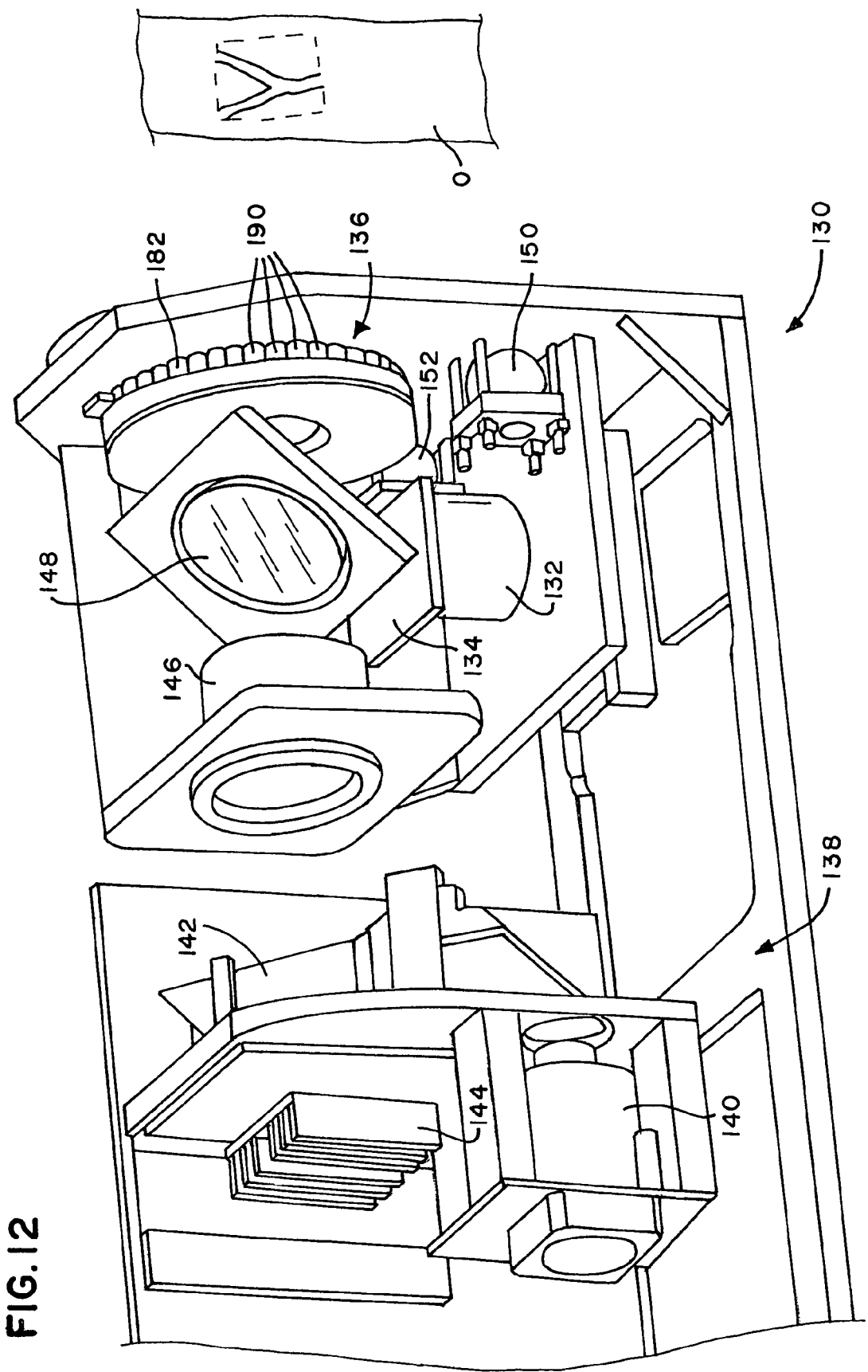
FIG. 12 is a perspective internal view of a third-version of the imaging system of the present invention.

A third preferred embodiment 130 of the imaging system is shown in FIG. 12. The near-infrared illumination A well-known CCD camera with lens 132 is used as the imaging device, as in all embodiments. A second polarizing filter 134 is interposed between the CCD camera and the reflected light from the viewed object, as previously described for earlier embodiments, so as to reduce specular reflection from the surface of the object. The illumination source, first polarizing filter, holographic illumination diffuser ring, and optically-neutral glass cover, all generally at 136, are best described below in the discussion of the fourth embodiment of the imaging system shown in FIGS. 13 and 14, which has the same structure 136 which is shown in cross-section for that embodiment.

As with all embodiments, the third preferred embodiment includes a well-known video projector 138 or so-called "light engine" for projecting a visible image onto the object O under examination. A desirable feature of the video projector 138 is high output light intensity, because the intensity of the output of the projector's light is a determining factor in how well the projected image can be viewed under normal room illumination. Video projector 138 includes a high-intensity green LED light source 140 which emits light into well-known prism assembly 142, thereby causing the emitted light to fold back, by internal reflection within prism assembly 142, and be directed rearwardly toward well-known Digital Light Processing ("DLP") device 144, also known as a Digital Mirror Device ("DMD"), having an array of closely-packed small mirrors that can individually shift the direction of the light beam reflected therefrom so as to either cause the light beam to be directed toward the target object through well-known projection lens 146 or to cause the light beam to not be directed toward the target object, thereby turning the emitted light beam off on a pixel-by-pixel basis in a manner well-known to those skilled in the art. It shall be understood that prism assembly 142 permits a more compact apparatus for the various embodiments of the imaging system, and the use of such prism assemblies is well known to those skilled in the art of video projectors.

As with the prior-described embodiments, a well-known so-called "hot mirror" 148 is interposed at 45 degrees to intercept the infrared light reflected from the viewed object and reflect that infrared light downward to camera 132. "Hot mirror" 148 acts as a mirror to longer wavelengths of light (such as infrared light) but higher-frequency light, such as the green light from projector 138, passes through without reflection and toward the viewed object.

Imaging system 130 further has first and second lasers 150, 152 for ensuring that the target is properly located for in-focus viewing by camera 132, as hereinafter described.

Figure 13:
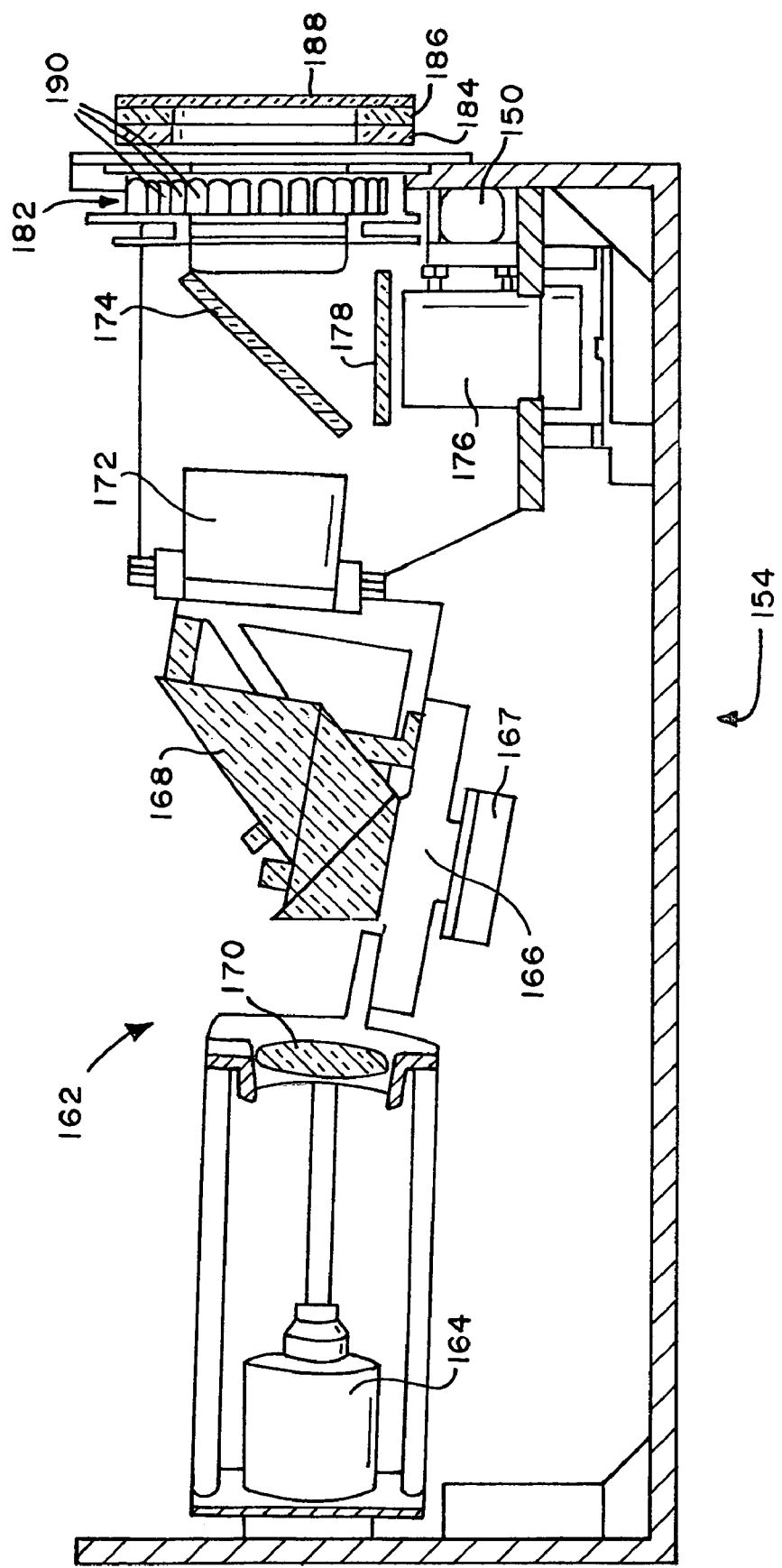
FIG. 13 is an internal view of a fourth version of the imaging system of the present invention with some parts shown in section for purposes of explanation.
Figure 14:
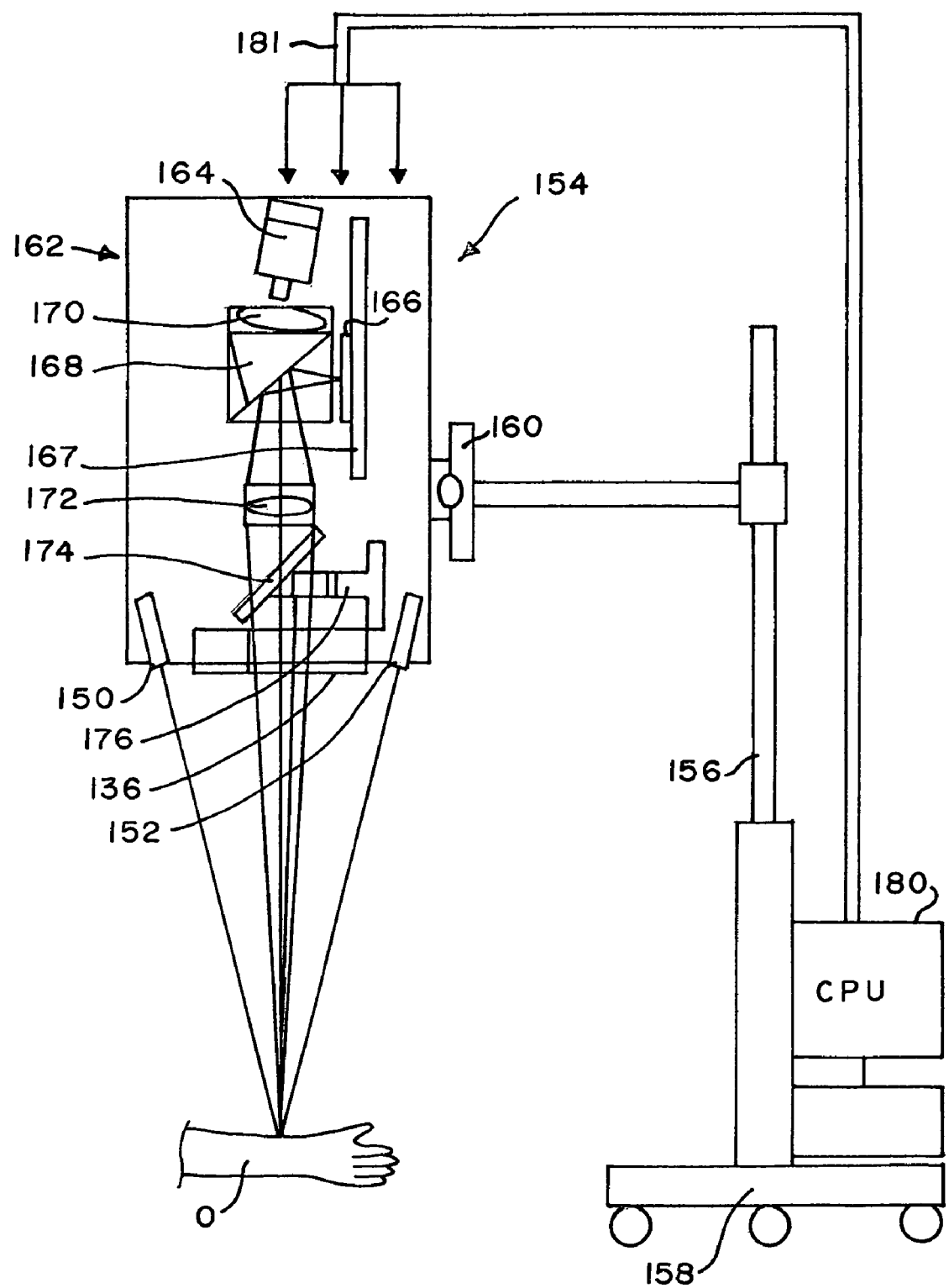
FIG. 14 is a diagrammatic view of the fourth version of the imaging system of the present invention.

Referring now to FIGS. 13 and 14, a fourth embodiment 154 of the imaging system of the present invention will now be explained.

Fourth embodiment 154 is mounted upon a pole 156 that extends upwardly from a mobile cart 158, allowing the imaging system 154 to be easily transported. A fine-focus stage 160 allows imaging system 154 to be raised or lowered so that it is properly positioned above the target object O. As with all embodiments, video projector 162 is provided with a 525 nm green LED illumination source ("photon engine") 164 for illuminating the DMD/DLP chip 166. A suitable photon engine 164 for use with the fourth embodiment is the Teledyne Lighting model PE09-G illuminator, having an output intensity of 85 lumens. DMD chip 166 may be a Texas Instruments part number 0.7SVGA SDR DMD chip having a resolution of 848×600 pixels and a mirror tilt angle of ten degrees and a frame rate of 30 Hz. Well-known prism assembly 168, as before, internally reflects the light from photon engine 164 toward DMD chip 166 and then directs the light reflected from DMD chip 166 toward object O. DMD chip 166 is controlled by a well-known drive electronics board 167 which may be made by Optical Sciences Corporation.

Interposed between photon engine 164 and prism assembly 168 is a condenser lens 170 such as a BK7 Bioconvex lens, part number 013-2790-A55, sold by OptoSigma, having a BBAR/AR coated surface coating for 425-675 nm light. As the projector light emerges from prism assembly 168, it passes through well-known projection lens 172, Besler part number 8680 medium format enlarger lens and then through well-known "hot-mirror" (high pass filter) 174, which reflects the received infrared light image from the object O through second polarizing filter 178 ant then to camera 176. A suitable camera 176 is the Firefly Camera, part number FIRE-BW-XX, sold by Point Grey Research, which uses a 640×480 CCD chip, part number Sony ICX084AL, and which communicates its images to computer ("CPU") 180 through an IEEE-1394 ("FireWire") interface. It should be noted that computer 180 has a number of interfaces signals 181 that communicate with the imaging system in a manner well-known to those skilled in the art. As briefly mentioned for the third embodiment, the fourth embodiment also has first and second lasers 150, 152 for ensuring that the target O is properly located for in-focus viewing by camera 176.

As with third embodiment 130 shown in FIG. 12, and with reference to FIGS. 12, 13, and 14, fourth embodiment 154 has an assembly 136 that includes infrared illumination source 182, first polarizing filter 184 (which is ring-shaped with a center hole therethrough so as not to affect the projected image from projector 162 or the viewed image of the object), holographic illumination diffuser ring 186 (which likewise has a center hole therethrough for passage of the projected image from projector 162 and of the viewed image of the object) and which diffuses the light from LEDs 190, and optically-neutral glass cover 188. Infrared illumination source 182 is a group of LEDs preferably arranged in a select pattern, such as a circular ring having a centrally-disposed hole through which the projected image and the viewed object's image passes. The LEDs are preferably 740 nm near-infrared LEDs 190 that illuminate the object O, and research has determined that such a structure provides sufficient diffused infrared light for satisfactory illumination of object O.

Referring to FIG. 15, a fifth embodiment 192 of the imaging system of the present invention will now be explained. The significant difference between this fifth embodiment and the other embodiments is that the fifth embodiment does not provide an integral diffuse infrared light source (e.g., illumination source 182 with a ring of LEDs 190) for illuminating the object, but instead views the object as illuminated by ambient light L (or the sun S) that has a broader spectrum than the integral diffuse infrared illumination sources heretofore disclosed. While ambient light has some infrared spectral components and is quite diffuse, those infrared spectral components are generally of lower intensity than the infrared light produced by the diffuse infrared illumination sources heretofore disclosed. Accordingly, a better (i.e., more sensitive) image device camera is required for this embodiment, with better optics than the previously-described embodiments.

Like the other embodiments, the fifth embodiment 192 includes video projector 162, including a green "photon engine" 164, prism assembly 168, projector lens 172, and DMD chip 166. To permit a compact design, fifth embodiment 192, as could any of the embodiments, includes a "fold mirror" 194 that folds the beam at a right angle within the projector between the photon engine 164 and prism assembly 168. Also like the other embodiments, fifth embodiment 192 includes a "hot mirror" 174.

Fifth embodiment 192 further has an infrared filter 196 interposed in the optical path between the imaging device (camera 198) and object O so as to filter out all but the infrared component of the image viewed by camera 198. Camera 198 is preferably a Basler CMOS camera, model A600-HDR, made by Basler Vision Technologies of Germany, which has an IEEE 1394 ("FireWire") interface and allows capture of images with up to a 112 dB dynamic range. An advantage of the fifth embodiment is that it can be (and should be) used in a brightly-illuminated room.

Experimental testing has revealed that some persons have arms or legs that are so covered with surface hair that it is difficult to see with clarity the projected subcutaneous structure that is projected onto the surface of the skin. Investigation has revealed that all hairs, even white hairs, look black in the near infrared. Hence, image processing is performed on the received image in order to remove small dark artifacts, such as hairs, from the image while retaining larger dark objects to maintain the visibility of the veins. FIGS. 16a and 16b, taken together in sequence, are a program listing for artifact removal image processing of the received image. The same artifact removal procedure is performed twice, and then a well-known adaptive edge enhancement procedure is performed, such as, for example, unsharp masking, followed by a smoothing to clean up image artifacts produced by the hair removal. The program listing is well-commented and explains to those skilled in the art the image processing steps that are applied to the image.

The received image, having integer pixel values in the range (0 . . . 255) is converted to floating point values between 0.0 and 1.0, inclusive. The resulting image is then converted to smoothed (blurred) using a Gaussian convolution having a sigma of 8 pixels. This is a fairly small value of sigma, and leave small features, such as narrow hairs, in the resulting smoothed image. A "difference image" is created which is the original image minus the Gaussian-smoothed image, producing a zero-centered set of values from −1.0 to 1.0. Hairs, even white hairs, appear black in the near infrared, so negative pixel values are indicative of hairs, and those negative-value pixels are thus replaced with the corresponding pixels from the Gaussian-smoothed image. This is the first step in the processing of the received image. Next, an array of values is created for the image, such that all pixel locations where the original "difference image" was negative (the "hair" locations) are set to 1.0, and all other pixel locations are set to zero, thereby creating an array populated by 0.0 or 1.0 values, with every "hair pixel" having a value of 1.0 and all others having a zero value. The original image ("im1"), having pixel values ranging from 0.0 to 1.0, is then "boosted" at every "hair pixel" location by 0.015. Because this is a highly non-linear operation, the amount of "boost" if quite small, just 1.5%.

This same set of operations (Gaussian smoothing with a sigma of 8 pixels, creation of a difference image, identifying negative pixel locations, and "boosting" the image where negative pixels (small features and noise) are found) are performed again, and the resulting image is then smoothed again with a Gaussian convolution having a sigma of 64 pixels. A third difference image is created, which is the again-"boosted" image minus the smoothed image, and an image is created that is formed from the absolute value of every pixel in the third difference image. The resulting absolute value image is then smoothed with a Gaussian convolution having a sigma of 64 pixels, and the third difference image is then divided by the smoothed absolute value image, and the resulting divided image is smoothed with a Gaussian convolution having a sigma of 4 pixels.

The foregoing Artifact Removal algorithm allows the contrast to be set by the contrast of the subcutaneous vein (the subsurface structure of interest), ignoring the artifacts (hairs), and thereby prepares the image for adaptive unsharp masking edge enhancement to set the contrast of the final image. Parameters such as sigma values, thresholds, etc., may be varied depending on the age of the subject, degree of pigmentation, etc.

FIGS. 17a, 17b, 17c, 17d, 17e, and 17f, taken together in sequence, are a program listing in the C++ programming language for artifact removal image processing of the received image which is based upon the research/investigation program shown in FIG. 16a and FIG. 16b, but instead uses the Intel image processing library to perform the mathematical operations more quickly.

Figure 18:
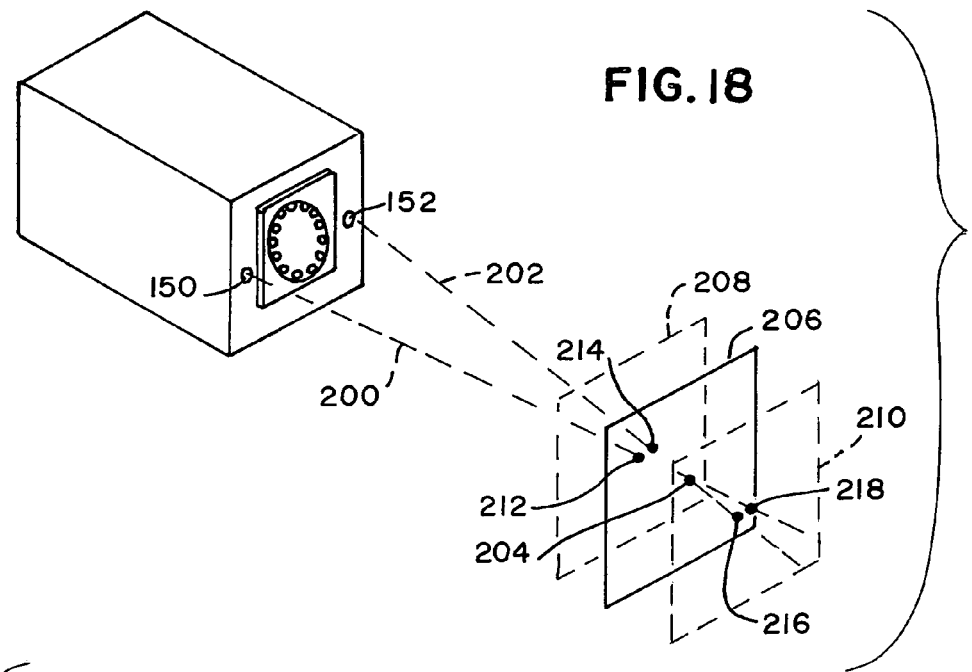
FIG. 18 is a diagrammatic perspective view showing how a pair of laser pointers are used to position the object to be viewed.

Any or all of the embodiments of the present invention preferably include a mechanism for keeping the image of the buried structure, as seen by the imaging device, in focus to the image device camera with a proper lens-to-subject distance thereto. As seen best in FIG. 18, a first embodiment of this mechanism uses a pair of lasers, 150, 152, each laser respectively emitting a beam 200, 202, with beams 200 and 202 being non-parallel with respect to each other and thus being directed toward the object from different angles, such that the two laser beams only converge to the same spot 204 and intersect when the target is at the proper lens-to-subject distance from the imaging device, as shown by the position of intersecting plane 206. If the target is closer to the apparatus than the proper lens-to-subject distance, as shown by plane 208, or if the target is further from the apparatus than the proper lens-to-subject distance, as shown by plane 210, the two laser beams will not intersect at a single point 204 but instead will appear on the surface of the object as a first pair of visible dots 212, 214 (for plane 208) or as a second pair of visible dots 216, 218 (for plane 210), indicating that the buried structure is not in focus to the imaging device camera, and that the distance from the object to the apparatus should be changed to bring the viewed image of the buried structure into focus. Lasers 150 and 152 may also be seen in FIGS. 12, 13, and 14. Suitable lasers for use with the present invention are the model LM-03 laser modules made by Roithner Lasertechnik, of Vienna, Austria.

A second embodiment of the target positioning mechanism adds a recognizable visible light pattern, such as a text border, independent of the buried structure being observed, to the projected image for mutual projection therewith. The projected recognizable pattern will only be recognized by the human viewer as being in focus on the surface of the target object when the target is at the desired distance from the projector, thereby causing the buried structure beneath the surface of the target to also be at the proper lens-to-subject distance from the imaging device. If desired, cartoon figures appealing to children could be provided as an incentive for children to properly position their body parts for viewing subcutaneous blood vessels, or a hospital's or clinic's logo or name could be used for the pattern. While the projected image of the buried structure is often somewhat blurred from image processing removal of artifacts, humans can quickly tell if a well-known or recognizable visible light pattern is out of focus. An advantage of this second embodiment of the target positioning mechanism, namely, the projection of a recognizable visible light pattern rather than the use of lasers, is that there is a possible hazard of injury, such as blindness, if proper safety precautions are not used with the lasers.

Figure 21:
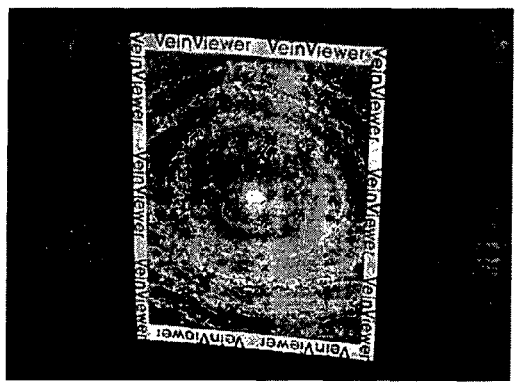
FIG. 21 is a photograph of a projected image having a text border therearound.

The photograph of FIG. 21 shows a projected image having a text border therearound.

Figure 22:
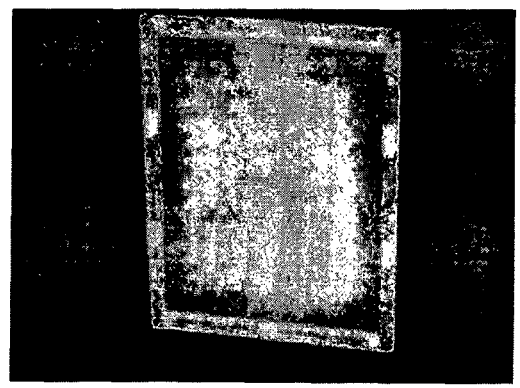
FIG. 22 is another photograph of a projected image having a text border therearound, similar to FIG. 21 but in which the viewed object has been moved out of position, showing how the text border becomes out-of-focus to indicate that the object is not positioned properly.

FIG. 22 is another photograph of a projected image having a text border therearound, similar to FIG. 21 but in which the viewed object has been moved out of position, showing how the text border becomes out-of-focus to indicate that the object is not positioned properly with respect to the image device camera.

Figure 23:
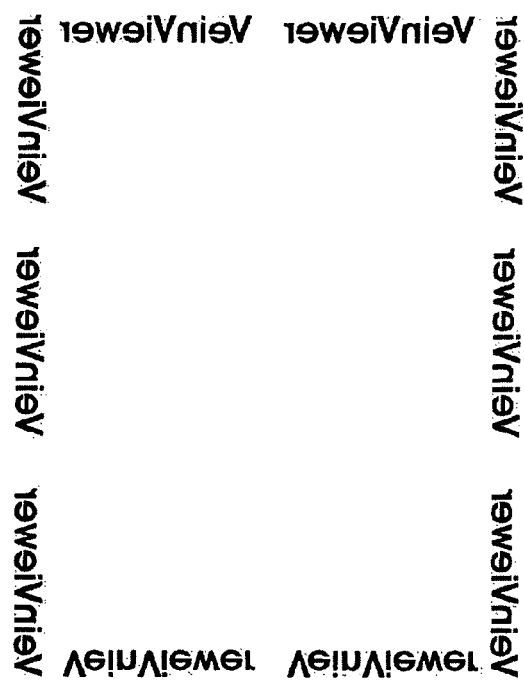
FIG. 23 shows a text border image that is combined with a projected image for joint projection onto the object to ensure proper positioning.

FIG. 23 shows a text border image that is combined with a projected image for joint projection onto the object to ensure proper positioning. Because of the image reversal that occurs in some embodiments of the invention as images reflect inside the prism structure heretofore described, this text border image is shown reversed but appears unreversed when projected. The projected image is appropriately cropped before combining with the text border so that the text border remains sharp and distinct when projected.

Figure 24:
FIG. 24 is a photograph of a processed image of subsurface veins projected onto a hand by the present invention, similar to FIG. 20 (which omits the text border) and FIG. 21 but showing how the text border becomes out of focus to indicate that the hand is not positioned properly.

FIG. 24 is a photograph of a processed image of subsurface veins projected onto a hand by the present invention, similar to FIG. 20 (which omits the text border) and FIG. 21 but showing how the text border becomes out of focus to indicate that the hand is not positioned properly.

Figure 19:
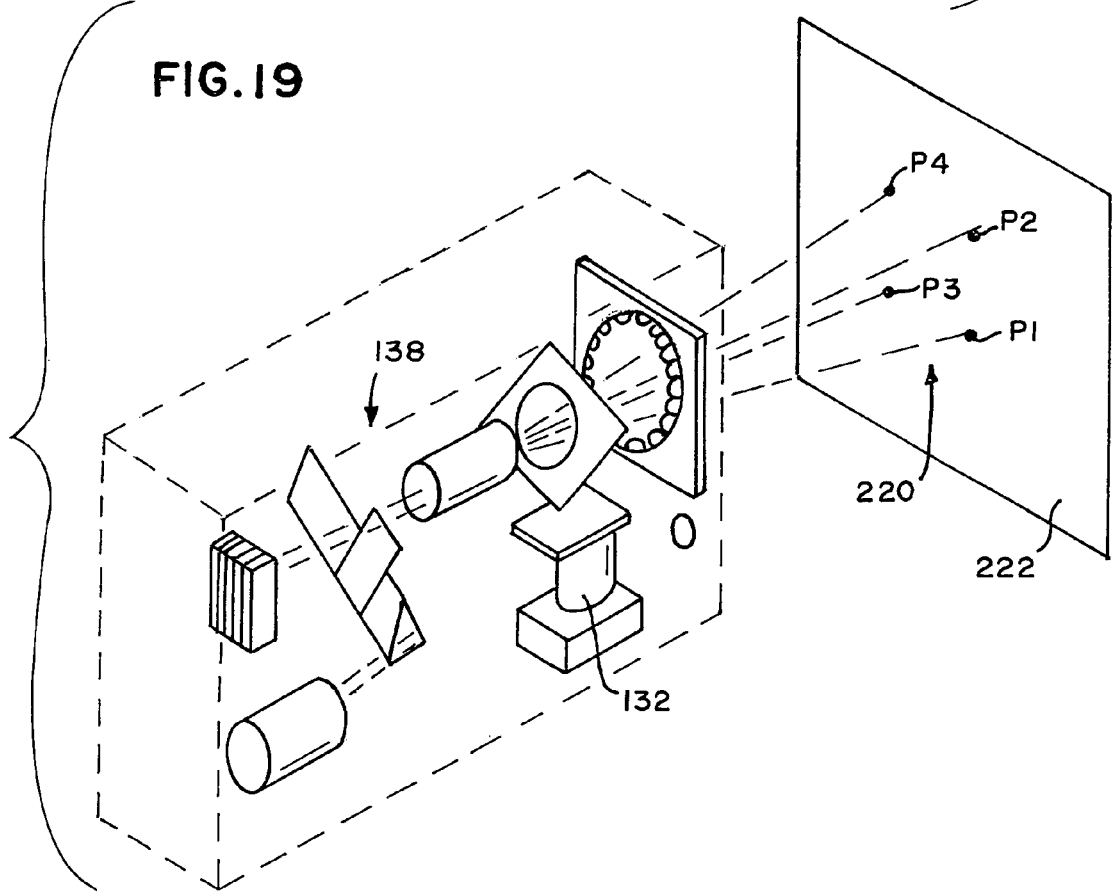
FIG. 19 is a diagrammatic perspective view showing the calibration procedure for the imaging system of the present invention.
Figure 25A:
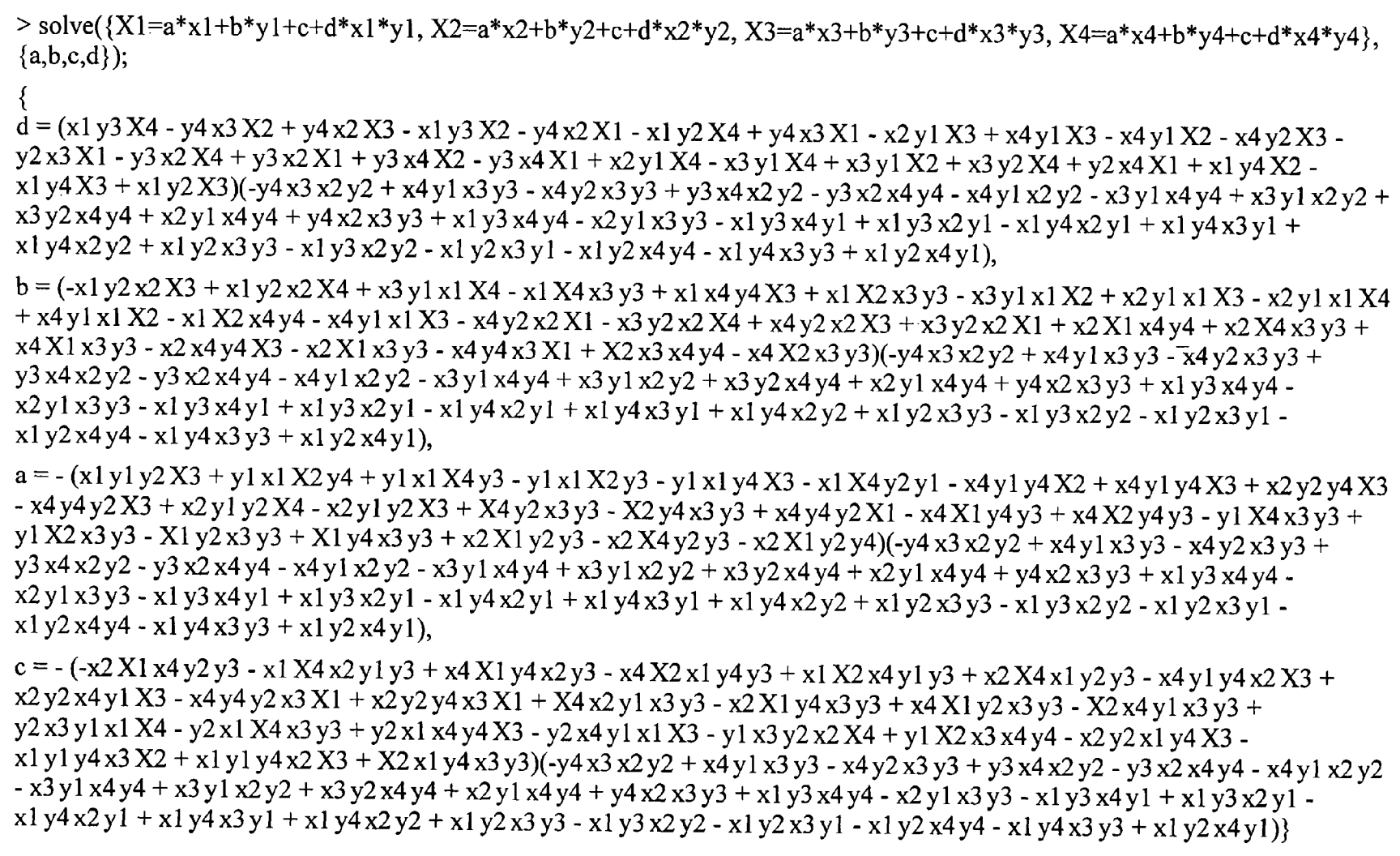
Figure 25B:
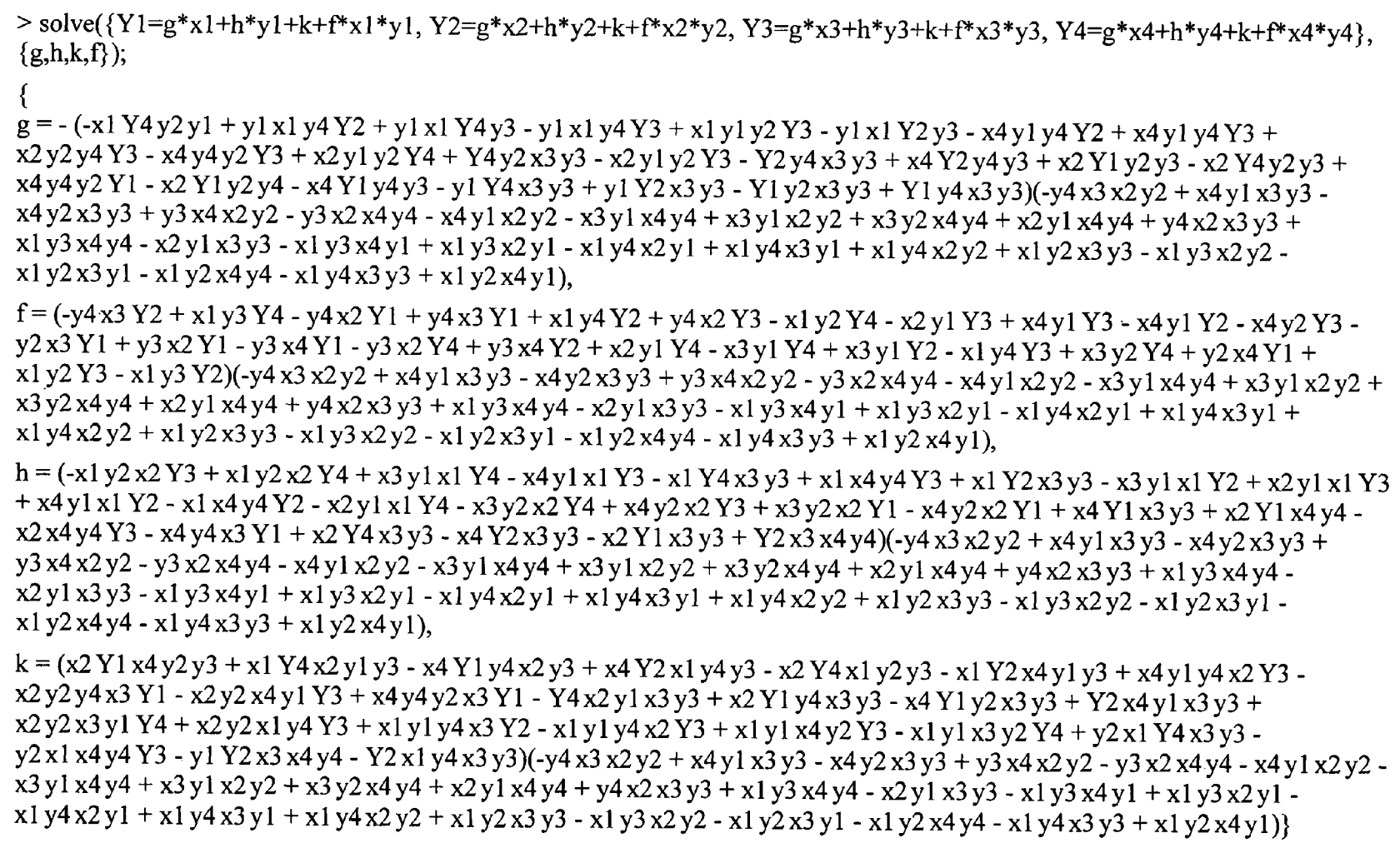

As shown in FIG. 19, a calibration method is provided wherein the video projector 138 (or 162, or any of the projector of the present invention) projects a green target pattern 220 onto a fluorescent screen 222, which converts the projected four-dot green target pattern 220 into deep red light that is visible by the infrared imaging device 132. A computer program records the observed position of the viewed pattern of four projected dots P1, P2, P3, and P4, in Cartesian coordinates, i.e., (x1, y1), (x2, y2), (x3, y3), and (x4, y4), versus the desired or "true" position of the dots if alignment were correct, i.e., (X1, Y1), (X2, Y2), (X3, Y3), and (X4, Y4), and calculates calibration coefficients (a, b, c, d, g, h, k, f) to be used in the bi-linear transformation equations (the arguments to the "solve" function in FIG. 25a and FIG. 25b) to correct magnification, rotation, and translation misalignment between the imaging device and the projector. FIG. 25a and FIG. 25b show the use of the MAPLE 9 computer equation solving program to solve for the bilinear transformation coefficients as a function of the values measured during calibration. These calibration coefficients are used during operation of the device to transform the coordinate system of the image (x, y) into the corrected coordinate system (X, Y) necessary to produce a calibrated image. FIG. 26 shows how these coordinates, once calculated during calibration, are used as parameters to a well-known image processing library mathematical routine provided by the integrated circuit company Intel for use with its processors, to achieve high performance image alignment correction using the bilinear transformation equation. The run-time calculations are done using scaled integer arithmetic, rather than floating point arithmetic, for faster processing of the image.

The calibration procedure projects a test pattern 220, consisting of four dots P1, P2, P3, and P4, each having a 25-pixel radius (as viewed by the imaging device camera) at the corners of a rectangle having dimensions of 320×240 pixels rectangle (as viewed by the imaging device camera), onto the fluorescent. For example, the camera 132 might have a resolution of 640×480 pixels, whereas the projector 138 might have a resolution of 1024×780 pixels. Experimental testing for dot radii varying from 4 to 50 pixels showed that the standard deviation of 100 samples decreased rapidly from a dot radius of 5 pixels to about 25 pixels, and then decreased much more slowly out to a radius of 50 pixels.

To practice the calibration method of the present invention, a test pattern of four spaced-apart dots P1, P2, P3, and P4 is projected within a first spectrum, preferably using green light, onto a fluorescent screen 222, which then fluoresces and produces light within a second spectrum, preferably light adjacent or within the infrared spectrum, such as red light, that is visible to the image device camera 132, even through the infrared transmitting filter through which the image device camera views its target object. Calibration software then measures the observed position of the four dots and computes the correction coefficients (a, b, c, d, g, f, h, k) for the bi-linear transformation equation, and then uses those coefficients as parameters to the bi-linear transformation in order to correct misalignment errors (rotation, translation, and magnification) between the image device camera and the projector by warping the image prior to projection so that the projected image is corrected for misalignment. It should be noted that this procedure allows for correction of magnification errors that are different in the horizontal and vertical directions, and also allows for correction of translation errors that are different in the horizontal and vertical directions.

Testing has shown that this calibration procedure can correct misalignments as great as +/−25.4 mm to within about half of the image camera's pixel size The alignment is best for image portion near the test pattern's four dots, but remains remarkably good over the entire image.

It should be understood that features of any of these embodiments may be used with another in a way that will now be understood in view of the foregoing disclosure. For example, any embodiment could choose to illuminate the object using infrared components within ambient lighting, rather than providing a separate diffuse infrared light source, and/or could choose between a laser target positioner and a recognizable pattern that is combined with the projected image of the buried structure for maintaining a desired distance from the image device camera to the object.

Although the present invention has been described and illustrated with respect to a preferred embodiment and a preferred use therefor, it is not to be so limited since modifications and changes can be made therein which are within the full intended scope of the invention.

What is claimed is:

1. An apparatus to enhance the visibility of a subcutaneous blood vessel beneath the surface of an object, the apparatus comprising:
   an imaging device configured to receive diffuse light reflected from the object and configured to produce an image, wherein the light reflected from the object originates as broad-spectrum ambient light or as diffuse light directed at the object; and
   a video projector configured to project a visible light image of the subcutaneous blood vessel onto the surface of the object, wherein the received diffuse light reflected from the object is coaxial with the projected visible light image wherein said projected visible light image includes a recognizable added pattern that is independent of said subcutaneous blood vessel.

2. The apparatus of claim 1 wherein said added pattern is a text border.

3. An apparatus to enhance the visibility of a subcutaneous blood vessel beneath a surface of an object, the apparatus comprising:
   an imaging device configured to receive diffuse light reflected from the object and configured to produce an image, wherein the light reflected from the object originates as broad-spectrum ambient light or as diffuse light directed at the object; and
   a first laser having a first emitted beam and a second laser having a second emitted beam, said first emitted beam and said second emitted beam being non-parallel with respect to each other and said first and said second emitted beams intersecting at a desired target distance from said apparatus at which, when the intersection of said first and said second emitted beams is visible upon the surface of the object, said subcutaneous blood vessel is in focus to said imaging device.

4. The apparatus as recited in claim 3, additionally comprising a video projector for projecting a visible light image of the subcutaneous blood vessel onto the surface of the object, wherein the received diffuse light reflected from the object is coaxial with the projected visible light image.

5. A method for enhancing the visibility of a subcutaneous blood vessel beneath a surface of an object, comprising the steps of:
   (a) providing an imaging device for receiving diffuse light reflected from the object, wherein the light reflected from the object originates as broad-spectrum ambient light or as diffuse light directed at the object;
   (b) producing a received image; then
   (c) removing small dark artifacts from the received image while retaining larger dark objects in the received image to produce a processed image; then
   (d) projecting the processed image onto the surface of the object in the visible spectrum, wherein the projection of said processed image is properly aligned such that said reflected diffuse light is coaxial with the projected processed image, resulting in the projected processed image accurately overlaying the corresponding subcutaneous blood vessel.

6. The method as recited in claim 5, additionally comprising, following the production of a processed image and before projecting the processed image, the step of performing adaptive edge enhancement upon the processed image.

* * * * *